United States Patent
Rasor et al.

(10) Patent No.: US 7,836,883 B2
(45) Date of Patent: *Nov. 23, 2010

(54) METHODS FOR TREATING RHINITIS AND CONJUNCTIVITIS

(75) Inventors: Ned S. Rasor, Cupertino, CA (US); Julia S. Rasor, Los Gatos, CA (US)

(73) Assignee: Capnia, Inc., Palo Alto, CA (US)

( * ) Notice: Subject to any disclaimer, the term of this patent is extended or adjusted under 35 U.S.C. 154(b) by 416 days.

This patent is subject to a terminal disclaimer.

(21) Appl. No.: 11/456,486

(22) Filed: Jul. 10, 2006

(65) Prior Publication Data

US 2006/0243276 A1    Nov. 2, 2006

Related U.S. Application Data

(60) Continuation of application No. 11/200,649, filed on Aug. 9, 2005, now Pat. No. 7,748,379, which is a division of application No. 09/614,389, filed on Jul. 12, 2000, now Pat. No. 7,017,573.

(60) Provisional application No. 60/185,495, filed on Feb. 28, 2000, provisional application No. 60/143,164, filed on Jul. 12, 1999, provisional application No. 60/148,736, filed on Aug. 16, 1999, provisional application No. 60/164,125, filed on Nov. 8, 1999.

(51) Int. Cl.
*A61M 11/00* (2006.01)

(52) U.S. Cl. .............................. 128/203.12; 128/203.22

(58) Field of Classification Search ............ 128/200.24, 128/203.12, 203.22, 203.29

See application file for complete search history.

(56) References Cited

U.S. PATENT DOCUMENTS

| | | | |
|---|---|---|---|
| 1,288,850 A | 12/1918 | Easly |
| 1,449,047 A | 3/1923 | Johnson |
| 1,742,605 A | 1/1930 | Lemoine |
| 2,574,028 A | 11/1951 | Fields et al. |
| 2,585,254 A | 2/1952 | Kochner |

(Continued)

FOREIGN PATENT DOCUMENTS

CH    247 873 A    3/1947

(Continued)

OTHER PUBLICATIONS

Hurst, "The Use of Carbon Dioxide in the Treatment of Vasomotor Rhinitis, Hay Fever, and Asthma," Proc R Soc Med., Feb. 24, 1931, pp. 441-442.*

(Continued)

*Primary Examiner*—Steven O Douglas
(74) *Attorney, Agent, or Firm*—Morrison & Foerster LLP

(57) ABSTRACT

Apparatus, methods, and kits for treating symptoms associated with common ailments, such as headaches, rhinitis, asthma, epilepsy, nervous disorders and the like, are provided. The apparatus comprises dispensers for carbon dioxide and other therapeutic gases. The methods comprise delivering small volumes of these gases to patients in a manner where the gas infuses into a body region in order to bathe the mucous membranes therein. It has been found that even very short exposure of patients to small volumes and high concentrations of such gases can provide significant relief from symptoms.

18 Claims, 12 Drawing Sheets

U.S. PATENT DOCUMENTS

| | | | |
|---|---|---|---|
| 2,651,303 | A | 9/1953 | Johnson et al. |
| 2,860,634 | A | 11/1958 | Duncan et al. |
| 2,920,623 | A | 1/1960 | Holt |
| 3,127,058 | A | 3/1964 | Johnston |
| 3,425,414 | A | 2/1969 | Roche |
| 3,513,843 | A | 5/1970 | Exler |
| 3,776,227 | A | 12/1973 | Pitesky et al. |
| 3,870,072 | A | 3/1975 | Lindemann |
| 3,934,585 | A | 1/1976 | Maurice |
| 3,974,830 | A | 8/1976 | LaVerne |
| 4,067,499 | A | 1/1978 | Cohen |
| 4,137,914 | A | 2/1979 | Wetterlin |
| 4,188,946 | A | 2/1980 | Watson et al. |
| 4,273,124 | A | 6/1981 | Zimmerman |
| 4,447,449 | A | 5/1984 | Marshall |
| 4,465,067 | A | 8/1984 | Koch et al. |
| 4,554,916 | A | 11/1985 | Watt |
| 4,694,850 | A | 9/1987 | Fumino |
| 4,934,359 | A | 6/1990 | Blaine |
| 5,099,834 | A | 3/1992 | Fishman |
| 5,123,442 | A * | 6/1992 | Geuy et al. ............ 137/495 |
| 5,262,180 | A | 11/1993 | Orlando et al. |
| 5,318,015 | A | 6/1994 | Masson et al. |
| 5,370,862 | A | 12/1994 | Klokkers-Bethke et al. |
| 5,431,155 | A | 7/1995 | Marelli |
| 5,485,827 | A | 1/1996 | Zapol et al. |
| 5,490,498 | A | 2/1996 | Faithfull et al. |
| 5,558,083 | A | 9/1996 | Bathe et al. |
| 5,562,644 | A | 10/1996 | McLeod |
| 5,570,683 | A | 11/1996 | Zapol |
| 5,807,357 | A | 9/1998 | Kang |
| 5,839,433 | A | 11/1998 | Higenbottam |
| 5,851,544 | A | 12/1998 | Penska et al. |
| 5,875,776 | A | 3/1999 | Vaghefi |
| 5,891,885 | A | 4/1999 | Caruso |
| 5,908,870 | A | 6/1999 | McLeod |
| 5,918,596 | A | 7/1999 | Heinonen |
| 5,938,590 | A | 8/1999 | Elliott |
| 5,941,241 | A | 8/1999 | Weinstein et al. |
| 5,951,538 | A | 9/1999 | Joshi et al. |
| 5,983,891 | A | 11/1999 | Fukunaga |
| 5,993,428 | A | 11/1999 | Hardge |
| 6,001,332 | A | 12/1999 | Garrett |
| 6,125,844 | A | 10/2000 | Samiotes |
| 6,258,032 | B1 | 7/2001 | Hammesfahr |
| 6,581,539 | B1 | 6/2003 | Rasor |
| 6,652,479 | B2 | 11/2003 | Rasor et al. |
| 6,959,708 | B1 | 11/2005 | Rasor et al. |
| 7,017,573 | B1 | 3/2006 | Rasor et al. |
| 2005/0228337 | A1 | 10/2005 | Rasor et al. |
| 2005/0279350 | A1 | 12/2005 | Rasor et al. |
| 2006/0076011 | A1 | 4/2006 | Rasor et al. |
| 2006/0172017 | A1 | 8/2006 | Rasor et al. |
| 2006/0237003 | A1 | 10/2006 | Rasor et al. |
| 2006/0237004 | A1 | 10/2006 | Rasor et al. |
| 2007/0017508 | A1 | 1/2007 | Rasor et al. |
| 2007/0039615 | A1 | 2/2007 | Rasor et al. |
| 2008/0132825 | A1 | 6/2008 | Rasor et al. |
| 2008/0169047 | A1 | 7/2008 | Connolly et al. |

FOREIGN PATENT DOCUMENTS

| | | |
|---|---|---|
| DE | 837 158 C | 4/1952 |
| DE | 14 91 660 A | 8/1969 |
| DE | 89 06 590 U | 10/1989 |
| DE | 4319612 | 12/1994 |
| DE | 19548652 | 10/1997 |
| EP | 0 198 708 A2 | 10/1986 |
| EP | 0 768 094 A | 4/1997 |
| FR | 2656218 A1 | 12/1989 |
| GB | 408 856 A | 4/1934 |
| JP | 08-224321 | 9/1996 |
| JP | 09-084876 | 3/1997 |
| WO | WO 91/08793 | 6/1991 |
| WO | WO 93/00951 A | 1/1993 |
| WO | WO 97/42992 | 11/1997 |
| WO | WO 99/29249 | 6/1999 |
| WO | WO 00/51672 | 9/2000 |
| WO | WO 00/57851 | 10/2000 |

OTHER PUBLICATIONS

Aizawa et al., "Role of Nitric Oxide Released from iNANC Neurons in Airway Responsiveness in Cats." Eur Respir J, 3(4):775-80, Apr. 1999.

Anton et al., "Psychophysical Examination of Pain Induced by Defined CO2 Pulses Applied to the Nasal Mucosa," Pain 49:53-60, 1992.

Can't Stop the Pain: Cluster Headaches Can Make Life Unbearable, Abcnews.com Jun. 13, 2001, retrieved from the Internet: <<www.abcnews.go.com/sections/GMA/GoodMorningAmerica/GMA010530Headaches_Cluster.html>>, 3 pages.

Cha et al., "Changes in Lung Volume and Breathing Pattern During Exercise and CO2 Inhalation in Humans," J Appl Physiol 62(4):1544-50, Apr. 1987.

Chatkin et al., "Nasal Nitric Oxide is Independent of Nasal Cavity Volume," Am J. Rhinol, 1999 13(3):179-84.

Declaration by Ned Rasor Regarding use of Invention Prior to Filing.

Dexter, "Rebreathing Aborts Migraine Attacks," Br. Med J (Clin Res Ed) Jan. 30, 1982, 28(6312):312.

Diamond "Migraine headache—its diagnosis and treatment." 13th Annual Practicing Physician's Approach to the Difficult Headache Patient, Rancho Mirage, CA, Feb. 5-19, 2000.

Echarri et al., "Sudden Deafness: Efficacy of a Therapeutic Protocol," [Article in Spanish] Acta Otorrinolaringol Esp 51(6):490-4, Aug.-Sep. 2000.

Faisy et al., Utilisation du Mélange Hélium-Oxygène en Pratique Pneumologique, Rev Mal Respir (1999) 16:1063-1073 [Article in French].

Fiermonte et al., "Cerebrovascular CO2 Reactivity in Migraine with Aura and without Aura,: A Transcranial Study," Acta Neurol Scand 92(2):166-9, Aug. 1995.

Fisher et al., "Resistance to Breathing During Exercise-Induced Asthma Attacks," Am Rev Respir Dis 101:855-896, 1970.

Fisher et al., "Site of Action of Inhaled 6 Percent Carbon Dioxide in the Lungs of Asthmatic Subjects Before and After Exercise," Am Rev Respir Dis 114(5):861, Nov. 1976.

Gillman et al, "Placebo and Analgesic Nitrous Oxide for Treatment of the Alcohol Withdrawal State," Br J Psychiatry 159:672-5, 1991.

Glovsky, "Upper Airways Involvement in Bronchial Asthma," Cur Opin in Pulm Med 4:54-58, 1998.

Goebel et al., "Rebreathing Aborts Migraine Attacks," British Medical Journal, vol. 284, p. 312, Jan. 30, 1982.

Grönroos et al., "A Selective Suppression of Human Pain Sensititvity by Carbon Dioxide: Central Mechanisms Implicated," Eur J. Appl. Physiol (1994) 68:74-79.

Grosser et al., "Olfactory and Trigeminal Event-Related Potentials in Migraine," Cephalaia Sep. 20, 2000:621-70.

Grosshans, "CO2 Gas Injection—Indications and Results," Z Gesamte Inn Med 42(33):667-70, 1987.

Guyton et al. Textbook of Medical Physiology. Ninth Ed., W.B. Saunders Co., Philadelphia, 1996, pp. 101, 203-204, 206-207, 454, 487, 515, 520-523, 527-23, 527-530, 541-544, 572-573, 617-619, 694.

Harrowes et al. "Fractional Administration of Carbon Dioxide in the Treatment of Neuroses", in Carbon Dioxide Therapy A Neurophysiological Treatment of Nervous Disorders. Second Edition. LJ Meduna Ed, Charles C. Thomas publisher, Springfield, IL 1958, pp. 294-305.

Hollman et al., "Helium-Oxygen Improves Clinical Asthma Scores In Chidren with Acute Bronchiolitis," Crit Care Med 26(10):1731-6, Oct. 1998.

Hummel et al., "Comparison of the Antinoclception Produced by Two Oral Formulations of Ibuprofen: Ibuprofen Effervescent vs. Ibuprofen Tablets," Eur. J. Clin Pharmacol (1997)52:107-114.

Groth et al., "Intranasal Fenoterol in Asthmatic Subjects: An Alternative Route of Administration," J. of Clinical Immunology, Oct. 1984, 4 pages.

Jolliet et al., "Beneficial Effects of Helium-Oxygen Versus Air-Oxygen Noninvasive Pressure Support in Patients with Decompensated Chronic Obstruction Pulmonary Disease," Crit Care Med 27(11):2422-9, Nov. 1999.

Jozefowicz, "Neurologic Manifestations of Systemic Disease," Neurologic Clinics, 7(3):605-616, Aug. 1989.

La Verne, "Rapid Coma Technique of Carbon Dioxide Therapy" in Carbon Dioxide Therapy: A Neurophysiologic Treatment of Nervous Disorders, Meduna eds., Charles C. Thomas, Springfield, Illinois, pp. 269-292.

La Verne, "Rapid Coma Technique of Carbon Dioxide Therapy," Dis Nerv System 14(5): 141-144, May 1953.

Leake et al, "The Stimulating Effect of Carbon Dioxid Inhalations in Dementia Praecox Catatonia," Calif West Med 31(1):20-23, Jul. 1929.

Leake, "The Historical Development of Surgical Anesthesia," Sci Monthly 20:304-320, 1925.

Lipkin et al., "Migraine and Sudden Sensorineural Hearing Loss," Arch Otolarynhol Head Neck Surg (1987) 113:325-326.

Loevenhart et al., "Cerebral Stimulation," JAMA 92(11), 1929.

Loh et al, "Cardiovascular Effects of Inhaled Nitric Oxide in Canine Model of Cardiomyopathy," Ann Thorac Surg Surg (May 1999) 67(5):1380-1385.

Lorente De Nó, Chapter III: Carbon Dioxide and Nerve Function in A Study of Nerve Physiology, Studies of the Rockefeller Institute for Medical Research, 131:148-194, 1947.

Macrae "Carbon Dioxide in Pediatrics," in Carbon Dioxide Therapy A Neurophysiological Treatment of Nervous Disorders. Second Edition. LJ Meduna ed, Charles C. Thomas publisher, Springfield, IL, 1958, pp. 146-164.

Marcussen, "Studies on Headache," Archives of Neurology & Psychiatry (1950) 63:43-51.

Meduna LJ Ed, Carbon Dioxide Therapy A Neurophysiological Treatment of Nervous Disorders. Second Edition. Charles C. Thomas publisher, Springfield, IL 1958.

Meduna, "Alteration of Neurotic Pattern by Use of $CO_2$ Inhalations," J Nerv & Ment Dis, 108(5):373-379, Nov. 1948.

Meduna, "Pharmaco-Dynamic Treatment of Pyschoneuroses (A Preliminary Report)," Dis Nerv System 8(2), 1947.

Mischler et al., "Prolonged Antiociception Following Carbon Dioxide Anesthesia In the Laboratory Rat," Brain Research (1994) 640:322-327.

Moriarty, "Prognosis with Carbon Dioxide Therapy, Including the Epinephrine-Mecholyl Test (Funkenstein Test)", in Carbon Dioxide Therapy A Neurophysiological Treatment of Nervous Disorders. Second Edition. LJ Meduna Ed, Charles C. Thomas publisher, Springfield, IL, 1958, pp. 376-395.

Moriarty, "Carbon Dioxide Inhalation Therapy of Neuroses," J Clin & Exper Psychopath, (Sep. 1952), 13(3):181-194.

National Headache Foundation. A patients guide to migraine prevention & treatment, Chicago, IL, Aug. 1996.

Navarra et al., "Gaseous Neuromodulators in the Control of Neutroendocrine Stresss Axis," Ann N Y Acad Sci 2000 917:638-646.

Nielsen et al., "The Effect of CO2 on Peripheral Airways," Acta Physiol Scand 98(2):192-9, Oct 1976.

Sands, "Oxygen Therapy for Headaches," National Headache Foundation, 2002, retrieved from the Internet:<<www.headaches.org/consumer/topicsheets/oxygen.html>>, 2 pages.

Pagano et al., "A Comparison of Inhaled Nitric Oxide With Intravenous Vasodilators in the Assessment of Pulmonary Haemodynamics Prior to Cardiac Transportation," Eur J Cardiothorac Surg (1996) 10(12):1120-1126.

Qi et al., "An Experiment Study of Reversed Pulmonary Hypertension with Inhaled Nitric Oxide on Smoke Inhalation Injury," Chun Hua Wai Ko Chih (Jan. 1997) 35(1):56-58.

Ream et al., "Low-Dose Inhaled Nitric Oxide Improves the Oxygenation and Ventilation of Infants and Children with Acute, Hypoxemic Respiratory Failure," Crit Care Med 27(5):989-96, May 1999.

Rodarte et al., "Effect of Acute Exposure to CO2 on Lung Mechnanics in Normal Man," Resp Physiol 17:135-145, 1973.

Saqueton CB et al., "No Causes Perinatal Pulmonary Vasodilation Through K+-Channel Activation and Intracellular Ca2+ Release," Am J Physiol 276(6 Pt 1):L925-L932, Jun. 1999.

Schaeffer et al., "Oxygenation in Status Asthmaticus Improves During Ventilation With Helium-Oxygen," Crit Care Med (1999) 27(12):2666-2670.

Schenk et al., "Inhaled Nitric Oxide in a Patient with Severe Pulmonary Embolism," Ann Emerg Med 33(6):710-714, Jun. 1999.

Schuttauf et al.,"Duplex Ultrasound Examinations of Retinal Circulation After Inhalation of Various Mixed Respiratory Gases," Opthalmologe 95(4):225-8, Apr. 1998.

Silkoff et al., "Nasal Nitric Oxide: A Comparison of Measurement Techniques," Am J. Rhinol, 1999 13(3) 169-78.

Singh et al., "Effect of Yoga Breathing Exercises (Pranayama) on Airway Reactivity in Subjects with Asthma," Lancet 335:1381-3, 1990.

Sterling et al. Effect of CO2 and pH on Bronchoconstriction Caused by Serotonin vs. Acetylcholine. J. of Appl. Physiology, vol. 22, 1972.

Tang et al., "Effect of CO2 on Serotonin-Induced Contraction of Isolated Smooth Muscle," Clin. Research (1972) 20:243.

Telepchak, "Smoking Cessation: New Strategies and Opportunities for Pharmacists," American Druggist, vol. 214, No. 1, Jan. 1997, pp. 48-56.

Wilkinson, "Some Clinical Observations Pertaining to the Effects of Carbon Dioxide on the Biology of Mental Disease", in Carbon Dioxide Therapy A Neurophysiological Treatment of Nervous Disorders. Second Edition. LJ Meduna Ed, Charles C. Thomas publisher, Springfield, IL, 1958, pp. 168-201.

Wilmoth et al., "Preventing Complications of Mechnical Ventilation: Permissive Hypercapnia," AACN Clin Issues 7(4):473-81, Nov 1996.

Serber, "Yoga Cure for Headaches," YogaJournal.com, Jan./Feb. 1999, retrieved from the Internet: <<www.yogajournal.com/health/121.cfm>>, 4 pages.

Yoga Rx for Headaches, Yogabasics.com 2001, retrieved from the Internet <<www.yogabasics.com/articles/headaches.html>>, 2 pages.

Serber, "Yoga: A Cure for Headaches," Shared Vision Magazine, May 2001, retrieved from the Internet: <<www.shared-vision.com/old_site/y01m05/storyc01.html>>, 3 pages.

Zysk, "The Science of Respiration and the Doctrine of the Bodily Winds in Ancient India," J. of American Oriental Society 113.2 :198-213, 1993.

Partial European Search Report for EP Application No. 06019590, dated Oct. 24, 2007.

Casale, T.B. et al. (Jan. 2008). "Intranasal Noninhaled Carbon Dioxide for the Symptomatic Treatment of Seasonal Allergic Rhinitis," *J. Allergy Clin. Immunol.* 121(1):105-109.

Final Office Action mailed on Jan. 25, 2010, for U.S. Appl. No. 11/456,477, filed Jul. 10, 2006, 7 pages.

Non-Final Office Action mailed on Jun. 16, 2008, for U.S. Appl. No. 11/456,477, filed Jul. 10, 2006, 7 pages.

Non-Final Office Action mailed on Jun. 20, 2008, for U.S. Appl. No. 11/534,119, filed Sep. 21, 2006, 7 pages.

Non-Final Office Action mailed on Jun. 26, 2008, for U.S. Appl. No. 11/456,490, filed Jul. 10, 2006, 7 pages.

Non-Final Office Action mailed on Oct. 20, 2008, for U.S. Appl. No. 11/456,477, filed Jul. 10, 2006, 7 pages.

Non-Final Office Action mailed on Oct. 20, 2008, for U.S. Appl. No. 11/456,490, filed Jul. 10, 2006, 7 pages.

Non-Final Office Action mailed on Oct. 21, 2008, for U.S. Appl. No. 11/534,119, filed Sep. 21, 2006, 8 pages.

Non-Final Office Action mailed on Jul. 16, 2009, for U.S. Appl. No. 11/534,119, filed Sep. 21, 2006, 7 pages.

Non-Final Office Action mailed on Jul. 17, 2009, for U.S. Appl. No. 11/456,477, filed Jul. 10, 2006, 6 pages.

Non-Final Office Action mailed on Jul. 17, 2009, for U.S. Appl. No. 11/456,490, filed Jul. 10, 2006, 7 pages.

Non-Final Office Action mailed on Mar. 22, 2010, for U.S. Appl. No. 11/456,490, filed Jul. 10, 2006, 6 pages.

Non-Final Office Action mailed on Mar. 23, 2010, for U.S. Appl. No. 11/534,119, filed Sep. 21, 2006, 6 pages.

* cited by examiner $\tan \phi/2 \sim \phi/2 = d/x$
$d \sim \phi x/2$
$\phi \sim 2d/x = 115\, d/x$ deg

METHODS FOR TREATING RHINITIS AND CONJUNCTIVITIS

CROSS-REFERENCES TO RELATED APPLICATIONS

This application is a continuation of U.S. application Ser. No. 11/200,649 (now U.S. Pat. No. 7,748,379), filed Aug. 9, 2005; which is a divisional of U.S. application Ser. No. 09/614,389 (now U.S. Pat. No. 7,017,573), filed Jul. 12, 2000; which claims the benefit of U.S. Provisional Application Nos. 60/143,164, filed on Jul. 12, 1999; 60/148,736, filed on Aug. 16, 1999; 60/164,125, filed on Nov. 8, 1999; and 60/185,495 filed on Feb. 28, 2000, under 37 CFR §1.78. The full disclosures of each of these applications are incorporated herein by reference.

BACKGROUND OF THE INVENTION

1. Field of the Invention

The present invention relates generally to medical apparatus and methods. In particular, the present invention relates to methods and devices for delivering carbon dioxide and other gases to patients for relieving symptoms associated with headache (e.g., migraine headaches, tension-type headaches, cluster headaches), jaw pain, facial pain (e.g., trigeminal neuralgia), allergies (rhinitis and conjunctivitis), asthma, nervous disorders (e.g., epilepsy, Parkinson's), and other common ailments.

A walk through the headache and allergy section of any pharmacy quickly reveals that there is wide spread interest in remedies for relieving symptoms commonly associated with headaches, allergies, asthma, and other common ailments. The commonly available therapies include oral medicines, nasal sprays, oral inhalers, nasal inhalers, eye drops, and nose drops, and probably other devices and approaches that have been developed over the years. Still more possible therapies are available from the pharmacy with a prescription from a patient's doctor (e.g., injectables, inhalables). Despite the very large number of therapies which are available, no one therapy meets all patient needs, and many of the therapies suffer from very significant shortcomings. For example, present day therapies are slow-acting, have numerous adverse side effects (e.g., nausea, drowsiness, rebound headache from analgesic overuse, rebound congestion from decongestant overuse, dizziness, sedation, addiction, and numerous others), have low efficacy, and are contraindicated for a large portion of patients (e.g., those with hypertension, coronary artery disease, cerebrovascular disease, peptic ulcers, pregnancy, concurrent medications that would interact, children, elderly, and others). Suffice it to say that there is a continuing interest in providing improved methods and apparatus for treating such common symptoms and ailments.

The use of diluted carbon dioxide by inhalation for treating symptoms related to headaches, allergies, asthma, nervous disorders, and other common ailments was demonstrated in the 1940's and 1950's. The treatment protocols generally rely on breathing masks or other equipment for delivering relatively large volumes of dilute carbon dioxide for the patient to inhale through the mouth and/or the nose into the lungs until they become unconscious. The efficacy of this treatment depends upon the systemic effects of the inhaled gas and therefore require large volumes of gas. Typical carbon dioxide volumes inhaled were in the range from 0.5 to 25 liters of 30% to 70% carbon dioxide diluted in oxygen during a single treatment which was repeated several times a week for 25 to 50 treatments. While the use of inhaled carbon dioxide has proven to be quite effective for a number of indications, the wide spread use of carbon dioxide delivered in this manner never became popular. It is limited by the necessity of making the patient unconscious, the length of the treatment time and course, and the necessarily large, bulky non-portable gas cylinders and physician administration it requires. Most prior systems are so large and heavy they must be wheeled about using a dolly or a cart, and thus do not lend themselves to use outside of the hospital or home. While hand-held carbon dioxide dispensers have been proposed (for other purposes such as the treatment of hyperventilation), they are designed to deliver large volumes of dilute carbon dioxide for inhalation.

For these reasons, it would be desirable to provide improved apparatus and methods for treating the symptoms normally associated with headaches, allergies, asthma, and the like. Such apparatus and methods should provide small volumes of gas for convenient use away from the home, substantially immediate relief of symptoms, safety with few or no side effects, efficacy without requiring unconsciousness, efficacy in a large number of patients, therapy for those contraindicated for present day therapies, therapy without interaction with concurrent medications, low cost, a long life (in at least some embodiments), and permit the patient to administer the therapy and adapt the product usage for maximum comfort and effectiveness. At least some of these objectives will be met by the inventions described hereinafter.

2. Description of the Background Art

U.S. Pat. No. 3,776,227, describes a hand-held dispenser that delivers dilute carbon dioxide intended for the treatment of hyperventilation by inhalation. In addition, this hand-held dispenser is not designed to deliver carbon dioxide at high concentrations which are unbreathable. Other inhalation devices, systems, and methods for delivering carbon dioxide and other gases and aerosols to patients are described in U.S. Pat. Nos. 3,513,843; 3,870,072; 3,974,830; 4,137,914; 4,554,916; 5,262,180; 5,485,827; and 5,570,683.

Gas therapy for the treatment of headaches, allergies, asthma, and other conditions as well as associated physiology is described in the following references in the medical literature:

A. Carbon Dioxide Therapy

Diamond, S. Migraine headache—its diagnosis and treatment. 13$^{th}$ Annual Practicing Physician's Approach to the Difficult Headache Patient, Rancho Mirage, Calif., Feb. 5-19, 2000

Fisher H K et al., *Am Rev Respir Dis* 114(5):861, November 1976

Fisher H K et al., *Am Rev Respir Dis* 101:855-896, 1970

Gillman M A et al, *Br J Psychiatry* 159:672-5, 1991

Grosshans V A et al., *Z Gesamte Inn Med* 42(23):667-70, 1987

Harrowes W M C, Selinger Z Fractional administration of carbon dioxide in the treatment of neuroses, in *Carbon Dioxide Therapy A Neurophysiological Treatment of Nervous Disorders*. Second Edition. L J Meduna Ed, Charles C. Thomas publisher, Springfield, Ill. 1958

Jozefowicz R F *Neurologic Manifestations of Systemic Disease* 7(3):605-616, August 1989

LaVerne A A *Dis Nerv System* 14:5, 1953

Leake C D et al, *Calif West Med* 31:20, 1929

Loevenhart A S et al. *JAMA* 92(11), 1929

MacRae, D. Carbon dioxide in pediatrics, in *Carbon Dioxide Therapy A Neurophysiological Treatment of Nervous Disorders*. Second Edition. L J Meduna ed, Charles C. Thomas publisher, Springfield, Ill., 1958

Marcussen R M, Wolff H G, *Arch Neurol Psychiatry* 63:42-51, 1950
Meduna L J *Dis Nerv System* 8(2), 1947
Meduna L J *J Nerv & Ment Dis* 108:373, 1948
Meduna L J Ed, *Carbon Dioxide Therapy A Neurophysiological Treatment of Nervous Disorders*. Second Edition. Charles C. Thomas publisher, Springfield, Ill. 1958
Moriarty J D Prognosis with carbon dioxide therapy, including the epinephrine-mecholyl test (Funkenstein test), in *Carbon Dioxide Therapy A Neurophysiological Treatment of Nervous Disorders*. Second Edition. L J Meduna Ed, Charles C. Thomas publisher, Springfield, Ill., 1958
Moriarty J D *J Clin & Exper Psychopath* 13(3), 1952
National Headache Foundation. A patients guide to migraine prevention & treatment, Chicago, Ill., August 1996.
Rodarte J R et al., *Resp Physiol* 17:135-145, 1973
Singh V et al., *Lancet* 335:1381-3, 1990
Wilkinson W E Some clinical observations pertaining to the effects of carbon dioxide on the biology of mental disease, in *Carbon Dioxide Therapy A Neurophysiological Treatment of Nervous Disorders*. Second Edition. L J Meduna Ed, Charles C. Thomas publisher, Springfield, Ill., 1958
Wilmoth D F et al., *AACN Clin Issues* 7(4):473-81, November 1996
B. Nitric Oxide Therapy
Pagano D et al., *Eur J Cardiothorac Surg* 10(12): 1120-6, 1996
Ream R S et al., *Crit Care Med* 27(5):989-96, May 1999
Schenk P et al., *Ann Emerg Med* 33(6):710-4, June 1999
C. Helium Therapy
Hollman G et al *Crit Care Med* 26(10):1731-6, October 1998
Jolliet P et al *Crit Care Med* 27(11):2422-9, November 1999
Schaeffer E M et al *Crit Care Med* 27(12):2666-70, December 1999
D. Physiology
Aizawa et al., *Eur Respir J* 13(4):775-80, April 1999
Cha E J et al., *J Appl Physiol* 62(4):1544-50, April 1987
Fiermonte G et al. *Acta Neurol Scand* 92(2):166-9, August 1995
Glovsky M M *Cur Opin in Pulm Med* 4:54-58, 1998
Leake C D *Sci Monthly* 20:320, 1925
Loh E et al., *Ann Thorac Surg* 67(5):1380-5, May 1999
Lorente de No'R *Studies of the Rockefeller Institute* 131: 148-194, 1947
Nielsen T M et al., *Acta Physiol Scand* 98(2):192-9, October 1976
Saqueton C B et al., *Am J Physiol* 276(6 Pt 1):L925-L932, June 1999
Schuttauf F et al *Opthalmologe* 95(4):225-8, April 1998
Sterling G M et al., *J of Appl Physiol* 32(1):39-43, January 1972
Tang A et al., *Clinical Research* 20:243, 1972

SUMMARY OF THE INVENTION

According to the present invention, methods, apparatus, and kits are provided for relieving symptoms associated with a variety of common ailments, particularly headaches, rhinitis, asthma, and epilepsy. Specific symptoms include head pain, jaw pain, facial pain, sinus congestion, sneezing, itchy throat, itchy eyes, rhinorrhea, difficulty breathing, seizures, and the like. This list of ailments and symptoms is not meant to be exhaustive, and the present invention may find use with other disorders where infusion with the treatment gases described hereinafter are found to provide for symptomatic relief. The inventions allow delivery of a small volume of therapeutic gas at high concentration directly into the nasal passages locally without inhalation providing faster relief without the adverse side effects of systemic drugs that are ingested, injected, or inhaled.

The present invention relies on infusing or bathing the mucous membranes of a body region of a patient, e.g., nasal and/or oral and/or ocular, with a treatment gas that induces a therapeutic effect relieving symptoms. An exemplary treatment gas is carbon dioxide but other gases such as nitric oxide, oxygen, isocapnic mixtures of gaseous acids, helium, and the like, will also find use. The therapeutic gases (referred to herein as "therapeutic gases") may be used in a substantially pure form without other gases, active agents, or other substances that dilute the therapeutic gas or that have other biological activities. In other instances, however, the therapeutic gases may be combined with other gases, such as inert carrier gases, active gases, solids to form aerosols, liquid droplets to form aerosols, sprays, powders, or the like to potentiate (enhance) their effects. Conversely, these agents combined with the therapeutic gas can potentiate the effects of the therapeutic gas. In such instances, the therapeutic gases and mixtures may have biological activities in addition to the relief of symptoms accompanying common ailments, as described above. In all instances, however, the carbon dioxide or other principle therapeutic gas will be delivered in a quantity and over a time course that results in the reduction or elimination of the symptom that is being treated. A preferred aspect of the present invention is providing the patient with the ability to select a rate of infusive gas flow and total gas dose that are effective and tolerable for the particular patient, which flow rate and dose are generally much smaller than those employed in previous art.

The present invention provides for the desired symptomatic relief by infusing the treatment gas into a nasal and/or oral cavity without the patient necessarily inhaling the therapeutic gas. In particular, it has been found that by having the patient not inhale the therapeutic gas, i.e., substantially prevent passage of the therapeutic gas into the trachea or lungs by holding his or her breath or by breathing either nasally or orally via the route not being infused with the therapeutic gas, the volume of the body region being treated is significantly reduced. A relatively low volume of the carbon dioxide or other treatment gas can thereby be used to achieve the desired therapeutic effect. In addition, substantial exclusion from the lungs permits the use of the treatment gas at high (chronically unbreathable) concentrations, often being substantially pure approaching 100%, which is necessary to achieve maximum effective treatment via the nasal and oral mucosa. Furthermore, nasal or oral infusion of a chronically unbreathable mixture of an inert carrier gas with nitric oxide permits direct delivery of nitric oxide to the treated mucosa without the oxidation of nitric oxide that would occur if the carrier gas were a chronically breathable mixture of nitric oxide with air or oxygen.

In the case of mild headaches, rhinitis, or similar conditions, a total carbon dioxide volume as low as one cubic centimeter (cc) delivered over a time as short as one second may achieve adequate symptomatic relief. Of course, for more severe symptoms, such as those associated with migraine headache, the total treatment volumes of carbon dioxide and treatment times may be much greater.

Nasal and/or oral administration of concentrated carbon dioxide without inhalation may provide adequate symptom relief for asthma due to the physiologic phenomenon known as the nasobronchial reflex. In all cases, however, it is believed that the ability to successfully relieve the patient's symptoms depends primarily on the total volume of treatment gas delivered to the patient over a sufficiently long duration. That is, the rate at which the treatment gas is delivered has little effect, and generally the patient can use as rapid a delivery rate as the patient finds comfortable or tolerable in order to achieve a target total dosage and reduce the amount of time needed for treatment. Guidelines for dosages and treatment times for infusion into a nasal and/or oral cavity for common symptoms associated with particular ailments are set forth in the Dosage Guideline below.

TABLE I

DOSAGE GUIDELINE

| Condition | Flow Rate (cc/sec) | Treatment Time Typical (Range) (sec) | Total Dosage Typical (Range) (cc) |
|---|---|---|---|
| Allergic Rhinitis: | | | |
| Mild | 1-10 | 3 (1-5) | 10 (2-20) |
| Moderate | 1-10 | 15 (2-30) | 30 (2-60) |
| Severe | 1-10 | 50 (3-79) | 160 (12-350) |
| Tension-Type Headache: | | | |
| Mild | 1-10 | 5 (1-16) | 30 (1-80) |
| Moderate | 1-10 | 10 (2-16) | 50 (2-80) |
| Severe | 1-10 | 60 (24-135) | 300 (168-675) |
| Migraine Headache: | | | |
| Mild | 1-10 | 30 (15-50) | 80 (40-150) |
| Moderate | 1-10 | 60 (23-115) | 160 (65-345) |
| Severe | 1-10 | 85 (30-180) | 250 (90-540) |

The present invention also provides for the desired symptomatic relief of allergic eye irritation (e.g., conjunctivitis) by infusing the treatment gas over the eye, either behind a cupped hand over the eye or by other cup means that confine the therapeutic gas at high concentration over the eye for the treatment period. The treatment time and dose for treatment of the eye are similar to those for nasal and oral treatment.

A first aspect of the present invention provides methods for delivering a therapeutic gas, e.g., carbon dioxide, nitric oxide, oxygen, isocapnic mixtures of gaseous acids, helium, and the like to a human patient. The method comprises generating a flow of the carbon dioxide or other therapeutic gas, and infusing a mucous membrane or an eye with the flow of the gas. As described above, in order to limit and concentrate the infusion of the therapeutic gas for nasal and/or oral treatment, the patient usually refrains from inhaling the therapeutic gas while the nasal or oral mucous membrane is being infused or the patient breathes either nasally or orally via the route not being infused with the therapeutic gas. In this way, the volume of the nasal and/or oral cavity that is filled by the flowing therapeutic gas is minimized and the concentration of the gas maximized since the therapeutic gas does not need to fill the large capacity of the lungs to provide a therapeutic effect.

While it will be preferred not to inhale the therapeutic gas, the gases are not toxic and some passage of the gasses into the trachea and/or lungs will not significantly detract from the therapy. Moreover, with practice, many patients will be able to continue breathing ambient air through a nasal or oral route while simultaneously infusing the oral or nasal mucous membranes with the therapeutic gas. That is, in some cases, the patient may continue breathing through the mouth while infusing the nasal passages with the therapeutic gas or continue breathing through the nose while infusing the oral cavity with the therapeutic gas. Thus, in the first aspect of the present invention, the patient is required only to limit or inhibit passage of the therapeutic gas into the trachea and/or lungs in order to localize or concentrate the therapeutic gas in the nasal or oral passages being treated.

In particular embodiments, the therapeutic gas may comprise essentially pure carbon dioxide. By "essentially pure," it is meant that the carbon dioxide, or other therapeutic gas, is free from the significant presence of other gases, i.e., the total volume of gas will comprise at least 50% carbon dioxide, preferably at least 70% carbon dioxide, and more preferably 95% or greater. In addition to being free from other gases, the carbon dioxide will be free from other physiologically or biologically active components, such as drugs, surfactants, and other substances that, although present at relatively low concentrations, would have physiologic or biologic effect.

In other embodiments, however, the carbon dioxide, or other therapeutic gas, may be present in a carrier which would have a significant presence, i.e., the total volume of carbon dioxide will comprise at least 6% carbon dioxide, preferably at least 30% carbon dioxide, and more preferably 49%. The carrier may be inert or biologically active. Exemplary inert carrier gases include nitrogen, air, oxygen, halogenated hydrocarbons, and the like. In preferred embodiments, the therapeutic gases are generated at a flow rate in the range from 1 cc/sec to 20 cc/sec, preferably from 2 cc/sec to 10 cc/sec. For pediatric application, flow rates less than 1 cc/sec (e.g., 0.5 cc/sec) may be preferred. Infusion preferably comprises directing the flow of therapeutic gas into one nostril and allowing the flow to infuse through the nasal passages and pass outwardly through the other nostril. Such infusion will occur under the pressure of the therapeutic gas that is being released into the one nostril, i.e., the patient is not inhaling or otherwise causing the therapeutic gas to infuse through the nasal passages. In such nasal passage infusion protocols, the patient's mouth is closed in order to block exit of the gas through the mouth. In an alternative infusion protocol, the therapeutic gas is directed into the patient's mouth and allowed to exit through either or both nostrils. In still another infusion protocol, the therapeutic gas is directed into a nostril or both nostrils and exits through the open mouth. In the latter two protocols, both the oral mucous membranes and nasal mucous membranes are infused with the therapeutic gas. The patient should avoid breathing substantially through the oral or nasal passages being perfused with the therapeutic gas. It should be recognized that the patient can breathe through the mouth while perfusing the nasal passages, and can breathe through the nose while perfusing the oral cavity. Furthermore, the patient can take single breaths during a long infusion step without substantially changing the total infusion time in that step.

The treatment steps may occur as a single infusion or multiple infusions. The length of any particular infusion step will depend, among other things, upon the degree of relief the patient is experiencing, i.e., the patient may continue and/or repeat infusions until relief is achieved. Single infusion steps usually will be performed for a time in the range from 1 second to 20 seconds for rhinitis relief and 1 second to 60 seconds for headache relief, and more usually from 2 seconds to 15 seconds for rhinitis and 10 seconds to 30 seconds for headache. The infusing steps often will be repeated one, two, three, four, or more times in order to achieve the desired total treatment time set forth in the table above. Usually, methods will be performed with hand-held or other delivery devices which have an adjustable flow rate capability. That is, the devices may be adjusted to deliver relatively constant therapeutic gas flows at a particular value within the range from 1 cc/sec to 20 cc/sec. The methods may thus further comprise adjusting the gas flow to a level which the patient perceives is comfortable. After the gas flow is adjusted, a total duration of treatment may be determined based on the gas flow and the desired total amount of gas to be delivered. While such treatment flows and treatment times may initially be selected based on data, such as provided in Table I above, it will be appreciated that the patient will eventually learn what treatment flow rates, treatment times, and number of treatments lead to successful symptom relief for them personally. Indeed, in medical practice today, gas therapy is a "titrate to effect" therapy without a specified dosage.

A second aspect of the present invention comprises methods for generating a therapeutic dosage of carbon dioxide or other treatment gas. The methods comprise releasing from a hand-held dispenser a flow of therapeutic gas comprising from 1 cc/sec to 20 cc/sec of carbon dioxide. Preferably, the gas flow will consist essentially of carbon dioxide, i.e., be pure carbon dioxide as described above. Alternatively, however, the gas flow may comprise carbon dioxide present in a carrier gas, also as described above and/or with solid or liquid drugs or other substances. The hand-held dispenser will have an outlet suitable for delivering the gas to the patient. In a preferred embodiment, the outlet will be suitable for sealing in or against a human nostril. In an alternative embodiment, the outlet will be suitable for sealing in or against a human mouth. In another alternative embodiment, the outlet will be suitable for sealing around a human eye or both eyes. One or more treatment steps may be performed, with each step having a duration in the range from 1 second to 100 seconds, preferably from 2 seconds to 30 seconds, and often from 1 second to 20 seconds, depending on the condition being treated and on its severity. The total number of treatment steps will be selected depending on symptom severity. Typically mild symptoms require 1 or 2 treatment steps, moderate symptoms require 2 to 3 treatment steps, and severe symptoms require 3 to 8 treatment steps. The total number of treatment steps will be selected depending on the flow rate in order to provide a total target dosage of the carbon dioxide. Typically, the flow rates will be adjustable to a set point within the range from 1 cc/sec to 20 cc/sec. While such treatment flows and treatment times and number of treatment steps may initially be selected based on data, such as provided in Table I above, it will be appreciated that the patient will eventually learn the treatment regimen that leads to successful symptom relief for them personally.

In yet another aspect, the present invention comprises dispensers for delivering therapeutic gases to a patient. The dispensers comprise a container holding a volume of the therapeutic gas, typically carbon dioxide or any of the other therapeutic gases described above. The dispenser further comprises a flow regulator that releases a flow of the therapeutic gas from the container to an outlet that is adapted to seal against a human nostril, mouth, or eye. Thus, the dispensers will be useful for delivering the therapeutic gas to the nostril, mouth, or eye for infusion of a mucous membrane according to the methods generally described above. As in the methods described above, the therapeutic gas is preferably carbon dioxide, either substantially pure carbon dioxide or carbon dioxide present in a carrier gas or liquid and/or combined with other active or non-active substances. The flow regulator preferably will be adjustable so that the patient can select a flow rate in the range from 1 cc/sec to 20 cc/sec, or within the other ranges set forth above. In an exemplary embodiment of the dispenser, the container comprises a cylinder, the adjustable flow regulator comprises a turnable cap at one end of the cylinder, and the outlet comprises a nozzle in the cap. The regulator may be turned to open the dispenser and initiate a flow of the carbon dioxide or other therapeutic gas. By then appropriately turning the cap, the flow rate can be adjusted to the user's preferred rate, and the outlet then inserted into or around the appropriate patient's orifice, in order to initiate infusion according to the methods described above.

In a further aspect, dispensers of the present invention for delivering carbon dioxide to a patient comprise a container holding a volume of carbon dioxide under pressure. A flow regulator is provided on the container and releases a flow of carbon dioxide from the container at a rate in the range from 1 cc/sec to 20 cc/sec. Preferably, the dispenser further comprises an outlet, where the outlet may be adapted to seal against a human orifice. Usually, the carbon dioxide will be substantially pure, although in other cases may be present in a carrier gas or liquid or in combination with other active or non-active substances. In certain particular embodiments, the carbon dioxide is present in the container as a liquid, wherein relatively large volumes of carbon dioxide can be stored. In other instances, the carbon dioxide will be present in the container as a pressurized gas. While the latter dispensers will hold less carbon dioxide, they do not need to be as sturdy as the containers that hold liquid carbon dioxide at much higher pressures. Preferably, the flow regulators will be adjustable to set points within the flow rate range.

In yet another aspect, kits according to the present invention comprise a container holding a therapeutic gas and instructions for use setting forth any of the methods described above for delivering the gas to a patient. The container may comprise any of the preferred dispensers described above, and the instructions for use and container will usually be packaged together in a conventional medical device package, such as a tube, tray, pouch, box, or the like.

DESCRIPTION OF THE SPECIFIC EMBODIMENTS

Figure 1:
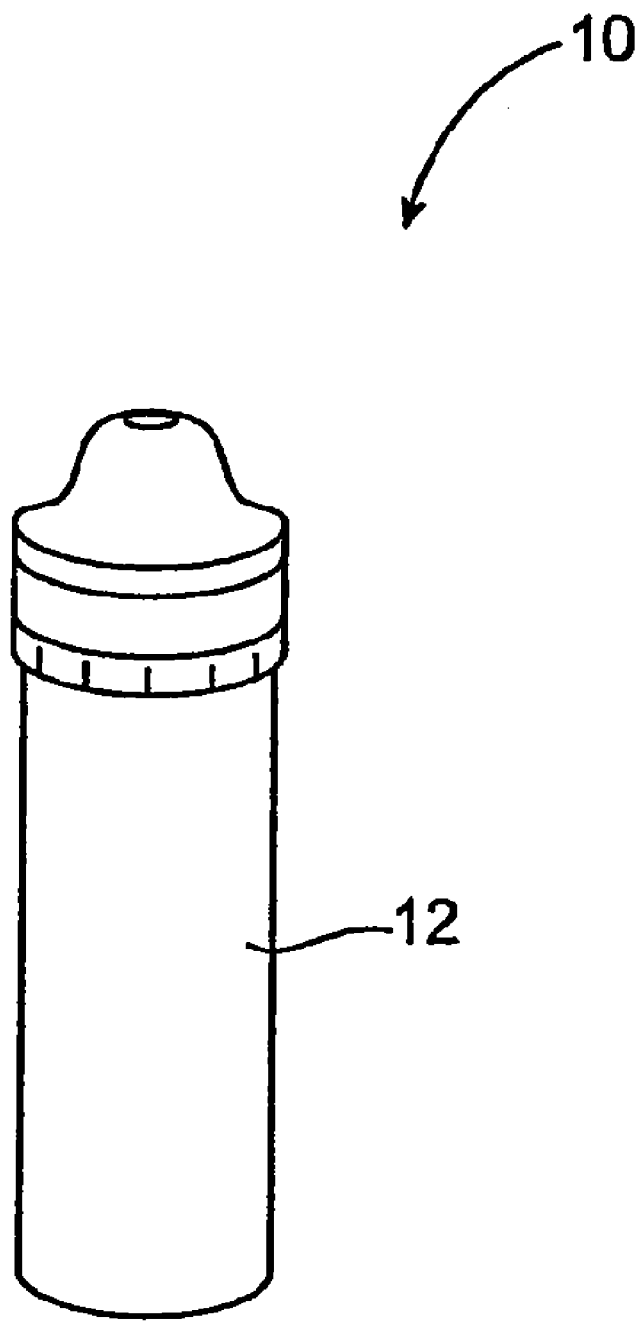
FIG. 1 illustrates a hand-held gas dispenser constructed in accordance with the principles of the present invention.

1. Treatment of Allergic Rhinitis and Headache. It has been found by the inventors, that bathing the mucous membrane of the nose, nasal passages, and mouth, with gaseous carbon dioxide for times as short as one second can suppress the onset of acute irritation of the mucosa caused by triggers such as airborne and contact-transmitted allergens and/or antigens. Furthermore, chronic inflammation of the mucosa and associated distress, caused by extended exposure to allergens and/or antigens, may be relieved within a few minutes by repeating such carbon dioxide applications. A possible mechanism of action of the above described local carbon dioxide treatment is the following. Creating a high concentration of carbon dioxide (hypercapnia) by infusing it into the nasal passages causes a very fast lowering of the pH (making more acidic) of the mucous membranes depressing the neuronal activity (inhibiting inflammatory mediator release such as histamine) of the nerves that supply the nasal mucous membranes and connect directly to the brainstem. Asthma is known to be a comorbid disease to allergic rhinitis. Carbon dioxide is known to relax both central and peripheral airways in asthmatic adults. In addition, it is known that oxygenation is improved in patients with status asthmaticus, chronic obstructive pulmonary disease, and bronchiolitis by inhalation of helium. Also, inhaled nitric oxide improves the oxygenation and ventilation of most children with acute, hypoxic respiratory failure. For this reason, these respiratory ailments can be reduced or relieved by administering the above-described treatment using carbon dioxide or helium or nitric oxide. Furthermore, headaches (e.g., migraine headaches, tension-type headaches, cluster headaches, jaw pain, facial pain) are thought to be due to triggers creating a hyperexcitability state of nerves releasing inflammatory mediators such as histamine and serotonin. For this reason, headaches can be reduced or relieved by administering the above-described carbon dioxide treatment. Epilepsy, also a nervous hyperexcitability state, is known to be a comorbid disease to headaches and antiepileptic medications are used for migraine prevention. For this reason, epilepsy can be reduced or relieved by administering the above-described carbon dioxide treatment. A convenient hand-held easily controlled dispenser of carbon dioxide has been found to be an adequate and optimum means for practicing this carbon dioxide application process. Furthermore, other gases such as nitric oxide, oxygen, helium, and others may be administered similarly as therapeutic gases via the convenient hand-held easily controlled dispenser.

Essential elements of successful suppression of irritating symptoms, pain, and inflammation through use of carbon dioxide are the convenient dispensing of the carbon dioxide or other therapeutic gas at a time, at a controlled flow rate, and for a duration selected by the user. Because of the ability of carbon dioxide to quickly or immediately suppress an acute attack, the means for carbon dioxide application should be available immediately, upon demand by the user, at the time when irritating symptoms appear upon exposure to a trigger. If circumstances do not permit such immediate application, the means for application must be available continuously to relieve the consequent inflammation and distress as soon as possible after the exposure when circumstances permit its use.

Furthermore, it is desirable that the user be able to conveniently but precisely and controllably select a rate and duration of carbon dioxide flow that lies between the lower limit of effectiveness and the upper limit of tolerance. It has been found that these limits are subjective, depending upon the personal sensitivities of the individual user, the degree and extent of the user's irritant reaction, and the site of carbon dioxide injection. Flows as low as 1 cc/sec for 1-2 seconds into the nose are effective for suppression of onset of acute allergic symptoms, whereas flows of 4-5 cc/sec for 5-10 seconds are typically selected for optimum relief from a mild chronic allergy attack. For severely inflamed mucosa and/or for injection into the mouth, flows as high as 10 cc/sec or higher for as long as 15 seconds or longer often are selected for optimum relief. For the treatment of tension and migraine headaches, the flow durations can be substantially longer, as generally set forth in the Dosage Guideline (Table I) above.

At low flow rates, the presence of the carbon dioxide produces a "tingling" sensation similar to that produced during drinking of carbonated beverages that inadvertently enter the nasal passages e.g., "bubbles up the nose". This is the effective rate and the tingling is a welcome sensation because it usually coincides with immediate relief of symptoms. Above a certain subjectively determined flow rate the sensation becomes unpleasant, which may be described as a "stinging" or "burning" sensation. At a still higher flow rate (maximum tolerable rate), the stinging sensation becomes intolerable and subjects remove the device from their nostril. It has been found that, for a few individuals, this tolerance level can be as low as 1-2 cc/sec for a second or less of injection into the nose. More typically, an injection rate of up to 10 cc/sec can be tolerated for 5 seconds or more into the nose by most users and into the mouth by almost all users. It must be noted, however, that the tolerance level depends strongly on the sequential phase of the application and on the degree of inflammation and/or pain at that phase. The tolerance level generally is lower (e.g., <3 cc/sec typically) at the onset of the first carbon dioxide injection, especially when there has been chronic inflammation and/or pain. After a few seconds the tolerance level rises substantially to the levels already discussed. In fact, the "stinging" sensation is described as a welcome immediate relief to the "tickling" sensation that causes sneezing and other distress during an allergy attack, i.e., analogous to relieving an itch by scratching a skin irritation. Similarly, the "stinging" sensation is described as a welcome immediate relief to the "pressure" sensation that causes pain and other distress during a headache attack.

Accordingly, the range of effective and tolerable flow rates of carbon dioxide is between 1 cc/sec and 20 cc/sec, preferably between 1 cc/sec and 10 cc/sec, and most preferably between 2 cc/sec and 10 cc/sec. The carbon dioxide flow is preferably regulated easily, controllably, and with rapid response within this range of flow rates by the user.

Most often the major site of general distress is the head, for which the preferred mode of carbon dioxide injection is directly into a nostril. While not inhaling the carbon dioxide, carbon dioxide is injected into a nostril and continued until full relief is obtained. This usually occurs when the carbon dioxide flow is detected exiting the opposite nostril and/or the mouth. With an allergy attack, often the nasal passages are blocked by swelling of the mucosa, in which case sufficient pressure automatically builds to open and perfuse the passage through each nostril separately. When both passages are clear, each can be perfused separately by holding one nostril closed while opening the mouth, or both can be perfused by closing the mouth and allowing the flow into one nostril to exit through the other. Frequently inflammation, swelling, and itching of the upper mouth accompany the irritant reaction to the allergen and/or antigen. In this case, it is most effective to inject the carbon dioxide through pursed lips directly into the mouth with exit through the nose while the breath is held. Specific techniques may be learned by experience and optimum procedures will depend on personal preference. The ability of the patient to optimize the treatment protocol is enabled by the fully adjustable flow rate and selectable injection site afforded by the devices of the present invention.

2. Initial Dispenser Embodiment. FIGS. 1-5 illustrate an initial dispenser embodiment 10 that was designed, built, and tested, with test results shown below. A subsequent presently preferred dispenser embodiment, having similar basic function but with improvements as described in Section 4 below, also was designed, built, and tested, with test results shown below. In the initial dispenser embodiment, a carbon dioxide cartridge housing 12 has screw threads 14 on the neck 15 of the cartridge. Such threaded carbon dioxide cartridges presently are marketed for use in other applications (available from Leland Limited, Inc., South Plainfield, N.J.), although the contents of such present carbon dioxide cartridges have not been qualified for administration to humans. The threaded carbon dioxide cartridge 12 is screwed into a threaded dispenser head 16, containing a perforating and flow-regulating needle 18 and flow dispensing ports 20. The threads employed, 28 per inch (11 per cm), are those commonly employed in commercial threaded cartridges.

The configuration of the initial dispenser embodiment as shown in FIGS. 1-5 provides an acceptable degree of flow regulation with acceptably low leakage through the valve seat formed by its penetration of the cartridge sealing cap. A hardened steel needle having the size and shape shown in FIG. 4A is sharp and strong enough to penetrate a plug-type cap 30 sealing the neck 15 of cartridge 12. Several designs of caps are composed of mild steel and are employed in commercial cartridges meeting industry safety standards, one of which is shown as the plug-type cap 30 in FIGS. 2,3,5 and 7. The cartridge and cap design features meeting these standards, including the required wall thickness and material strength of the cartridge and cap walls, are well known to those skilled in high pressure gas cartridge design, and have been widely accepted as being fully adequate for many years in mass-produced consumer products. Needle 18 having the dimensions set forth below, when employed with caps 30 having the critical dimensions set forth below, will provide both leak tight seals and optimum flow rates for the present invention. As shown in FIG. 3B, when the needle-bearing head 16 is fully screwed onto the carbon dioxide cartridge, the end of the cartridge encounters the surface in which the needle is mounted or another limit. The distance that the needle can penetrate the sealing cap 30 thereby is precisely limited, and the hole it thereby produces has precisely defined dimensions which control and limit the rate of carbon dioxide flow from the cartridge to within a desired flow range (e.g., 1-20 cc/sec) for safe and effective application. The needle 18 creates a pressure-type valve seat as it enters and penetrates the cap. A stop or limit, e.g., provided by engagement of the head 16 against the neck 15, prevents the needle from distorting or enlarging the seat (hole). Controlled flow occurs when the needle is controllably withdrawn from the seat, as shown in FIG. 3C.

It has been found that mounting the needle 18 in a head 16 material with a relatively high degree of elasticity, such as a plastic polymer, provides a degree of compliance sufficient to accommodate any off-axis "wobble" that occurs during rotation of the head and thereby avoids the associated non-circular and leaky penetration hole that occurs when the needle is mounted rigidly in a metal head. The elastic mount also provides compressive compliance that keeps the needle firmly seated after its repeated insertion into the orifice.

The configuration of the dispenser embodiment shown in FIGS. 1-5, having the carbon dioxide-containing cartridge screwed directly into the dispenser head, provides additional advantages. The amount of carbon dioxide contained in a convenient hand-held dispenser is thereby greatly increased over configurations that employ an external cartridge housing. Commercially produced cartridges with threaded necks are available in various sizes containing 8, 12, 16, 38 or more grams of carbon dioxide. The appropriate size employed in the dispenser embodiments described depends on the relative importance of cartridge size and number of treatment doses required for a particular use. For example, studies have shown that hand-held products for treatment of allergic rhinitis must provide hundreds of doses, which would require a relatively large carbon dioxide cartridge. In contrast, hand-held products for treatment of headache need to provide only a few doses, requiring a relatively small cartridge. Balanced against these requirements is the relative importance of size depending on the preferences of various users, e.g., for convenient carrying of the dispenser in a purse or pocket. The 16-gram size cartridge is a presently preferred compromise among these factors. The options readily available for head and cartridge designs having a standard thread in the embodiments described provide a high degree of design flexibility. Similarly, the relatively high simplicity and easy producibility of the dispenser head embodiments described permits fabrication of the dispensing head and cartridge as a single disposable device, especially with a molded plastic polymer head.

Figure 3A:
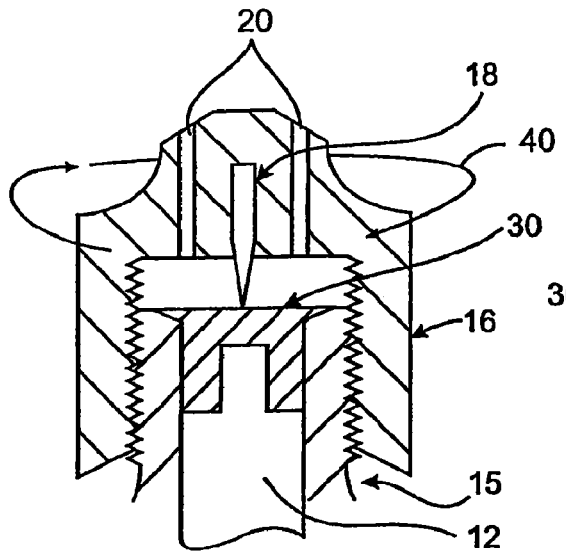
FIGS. 3A-3C are detailed cross-sectional views of the dispenser head and flow regulator of the dispenser of FIGS. 1 and 2.
Figure 3B:
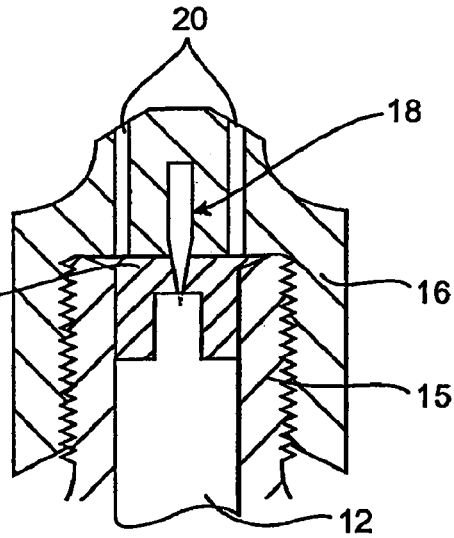
Figure 3C:
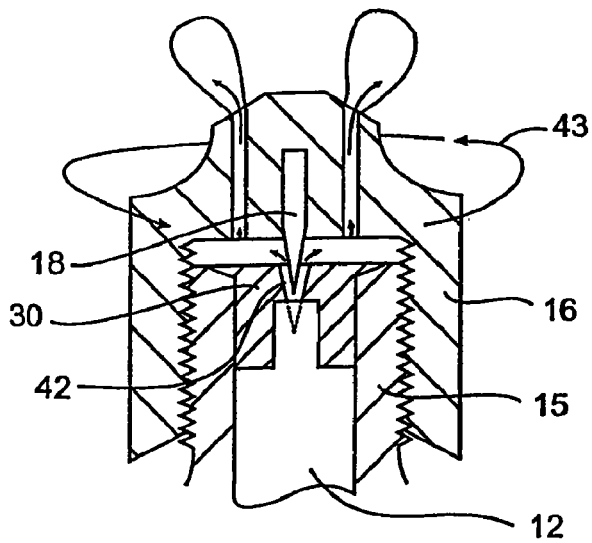
Figure 5:
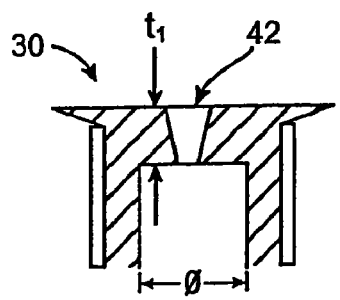
FIG. 5 is a detailed view of the penetrable cap positioned in the pressurized gas container of the dispenser of FIGS. 1 and 2, shown after penetration by the needle of FIG. 4A.

The dispenser 10 can be conveniently operated using the steps illustrated in FIGS. 3A-3C. In FIG. 3A, the dispenser head 16 is shown in its "shelf" condition where the head is fully elevated relative to the cartridge body 12 so that needle 18 lies above the exposed surface of cap 30. At this point, of course, the cap 30 has not been perforated. It will be appreciated that the head 16 may be completely removed and, indeed, the head 16 and cartridge 12 may be stored and/or distributed separately, where the head 16 may be disposable or reusable. When a patient desires to begin using the dispenser 10, the head 16 will be rotated in the direction shown by arrow 40 in FIG. 3A to cause the head 16 to lower relative to the cartridge body 12 and to cause needle 18 to penetrate into cap 30, as shown in FIG. 3B. By completely closing the cap 16 against the upper surface of the neck 15, as shown in FIG. 3B, the needle 18 will precisely define the penetration 42 having the desired geometry (defined by the geometry of the needle), as shown in FIG. 5. The dispenser 10 is then ready for use. Alternatively, the dispenser can be supplied with the needle having penetrated the cap. In this manner, quality control sampling of the contained gas can be performed at the manufacturing plant by twisting the dispenser head. A user can open the dispenser head 16 by rotating in the opposite direction, as indicated by arrow 42 in FIG. 3C. The dispenser head is rotated sufficiently to lift the needle 18 up out of the penetration 42 and cap 30. The degree to which the needle is removed from the penetration 42 will determine the flow rate of the gaseous carbon dioxide or other therapeutic gas. That is, the gap left between the outer surface of the needle 18 and the inner surface of the penetration 42 will be variable to create a variable annular flow area through which the gas can pass. The gas flow rate will thus depend on the degree to which the cap 16 has been rotated.

Figures 6, 7:
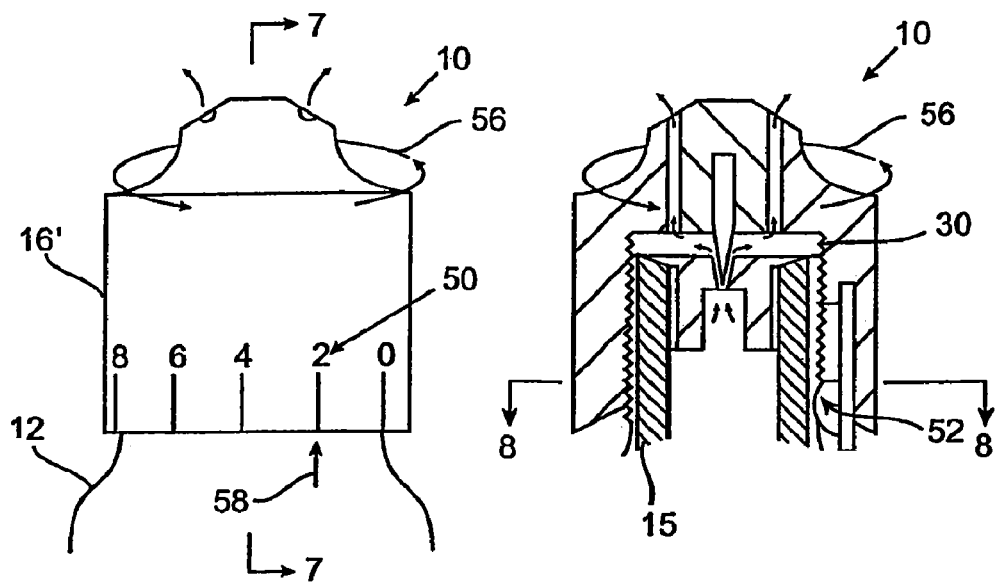
FIG. 6 illustrates a preferred embodiment for calibrating the flow regulator of FIGS. 3A-3C.
FIG. 7 is a cross-sectional view taken along line 7-7 of FIG. 6.
Figures 8, 9:
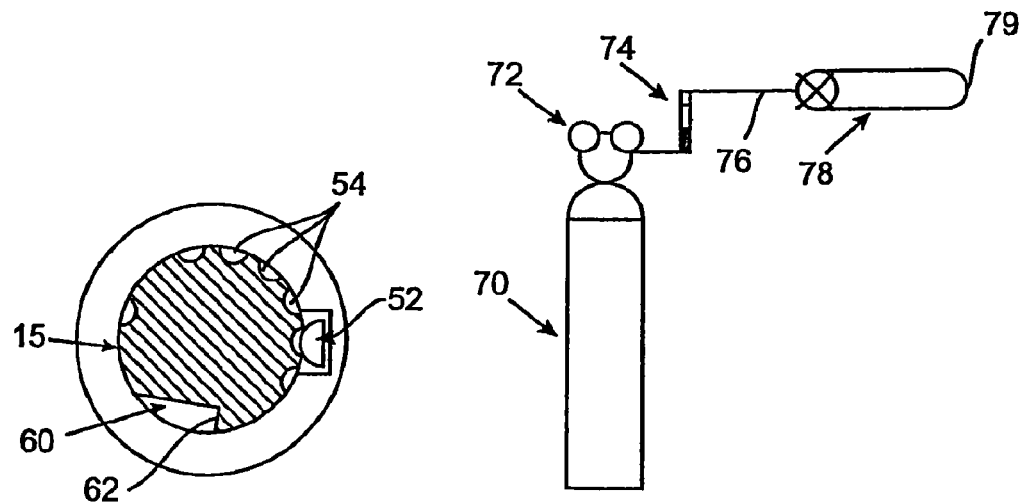
FIG. 8 is a cross-sectional view taken along line 8-8 of FIG. 7.
FIG. 9 is a schematic illustration of a hand-held gas dispenser connected to a large gas supply source.

Referring now to FIGS. 6-8 the dispenser 10 may be modified to have a calibrated dispensing head 16' with numbers 50 printed or engraved on its lower end to indicate flow rate set points. In a first embodiment, the numbers could be provided without further modification of the head 16 so that a user can dial in any flow rate at or between the designated numbers. In a second embodiment, the dispenser head 16' will be modified to have a spring arm 52 which is received in a plurality of detents 54 formed in the collar 94. The locations of the detents 54 are selected so that the dispenser head 16' will "click" into place for each of the set points indicated by numbers 50 on the dispenser head. To utilize the dispenser head 16', the user will turn the cap in the direction of arrow 56 until the flow rate number 50 is aligned with an indicator arrow 58 printed or embossed on the cartridge body 12. In addition to the visual alignment, the user will sense and hear when the spring arm 52 has entered the detent 54 that corresponds to the desired flow rate. In the most preferred embodiments, a notch 60 is formed in the collar 94. The notch 60 acts as a rotation-limiting stop so that the user cannot accidentally remove the dispenser head 16'. That is, as the spring arm 52 is rotated in the direction of arrow 56 it will eventually enter the notch 60. The abrupt wall 62 at the end of the notch will prevent continued rotation, in turn preventing accidental removal of the head. Of course, the presence of the spring arm 52 may prevent reuse of the rotational cap 16', so that the design of FIG. 6-8 will generally be intended to be disposable.

It should be apparent that methods other than rotation of the dispenser head can be used to controllably vary the flow through a perforation orifice; e.g., the needle can be moved axially by a lever arrangement to controllably accomplish the described perforation and flow regulation within the preferred range of flow rates described herein. Such an arrangement in a hand-held embodiment having a similar optimum degree of sensitivity and range of adjustment by the fingers as the rotation means described herein can achieve the same result.

Figure 9A:
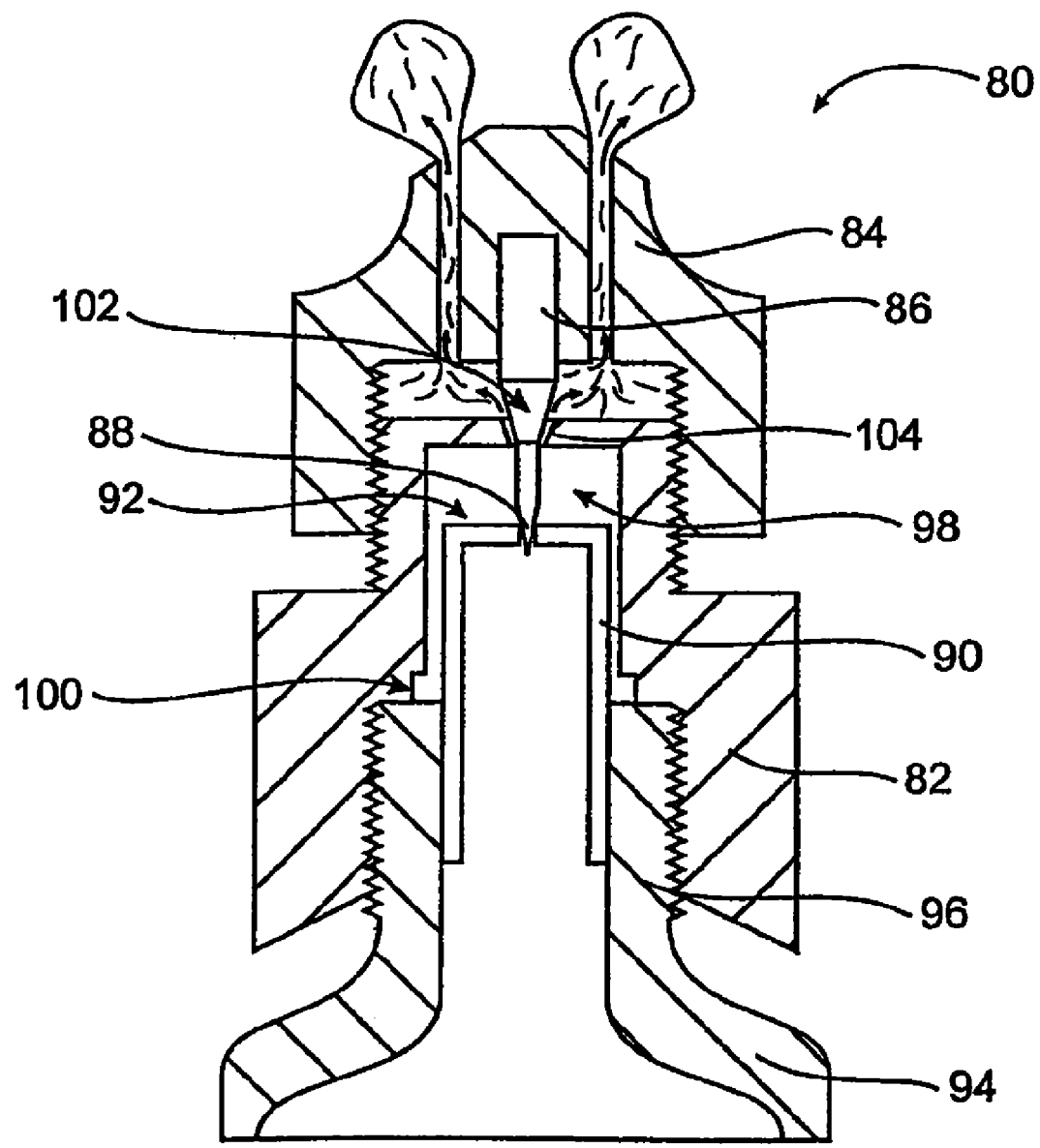
FIG. 9A illustrates an alternative construction for a dispenser head having separate puncture and flow-regulating means.

3. Embodiment with Separate Puncture and Flow Control Means. Referring now to FIG. 9A, an alternative dispenser head embodiment 80 will be described. The dispenser head 80 is similar to the embodiment described above with respect to FIGS. 1-5, except that the needle perforation and flow regulating aspects of the assembly are separated. In particular, the dispenser head 80 comprises a lower collar 82 and a flow-regulating cap 84 threadably mounted to an upper end of the lower collar. Needle 86 is secured in the lower portion of the flow-regulating cap 84 and includes two tapered regions. The first tapered region 88 acts as the needle tip which penetrates seal 90 which is mounted over the upper end 92 of a high pressure gas bottle 94. The seal 90 extends above a threaded neck 96 of the gas bottle 94. The lower collar 82 is threadably mounted over the threaded neck 96 in such a way that the seal 90 extends into a high pressure gas chamber 98 within the upper end of the lower collar 82. An O-ring seal 100 is provided to inhibit leakage of the high pressure gas.

Flow regulation in the dispenser head 80 is provided by the second tapered region 102 which is received in a valve seat 104 formed in the upper end of the lower collar 87. Rather than relying on needle penetration to form the flow control aperture, dispenser head 80 relies on a pre-formed conical valve seat 104 which mates with the tapered region 102 on the needle. In this way, the dimensions of both the seat 104 and the tapered region 102 may be carefully controlled in order to assure accurate gas flow control. Thus, when the flow regulating cap 84 is twisted to raise the cap relative to lower collar 82, the tapered region 102 will be lifted out of the valve seat 104. In this way, the flow regulation of the gas can be controlled. Additionally, sealing of the gas flow when the cartridge is to be turned off is provided by both seating of the tapered needle portion 102 in the seat 104 as well as seating of the needle tip in the penetration created in the seal 90. The use of the valve seat 90, which can be formed from a conventional hard metal, ceramic, or other valve material, can greatly enhance the useful life of the dispenser head 80. Thus, such designs may be particularly valuable for non-disposable units where the dispenser head 80 can be reused. Of course, the associated gas cartridge will be replaced whenever the gas being carried has been depleted.

4. Preferred Dispenser Embodiment. From the tests with the initial dispenser embodiment, several improvements were defined leading to a preferred embodiment that also was constructed and tested. It was found that the preferred dispensers of the present invention should enable precise but easy control of the flow rate over the desired flow ranges in a convenient hand-held configuration. In the specific preferred embodiment illustrated in FIG. 9B, it has been found that there is an optimum relationship between the rate of flow of carbon dioxide or other therapeutic gas selected by a user and the degree of rotation of the dispenser head relative to the cartridge that is required to obtain that flow. If the degree of rotation required is too small, it is difficult for the user to select the optimum rate of flow, i.e., the adjustment sensitivity is too coarse. If the degree of rotation is too large, the adjustment to the optimum flow rate requires more than one positioning of the thumb and forefinger that the typical user employs to rotate the head; i.e., the adjustment is awkward and its sensitivity is greater than required. In the latter respect, the mode of adjustment employed by many if not most experienced adult users is to hold the dispenser in the palm of one hand only with the third, fourth and fifth fingers and to rotate the dispenser head with the thumb and index finger of that hand.

Specifically, it has been found that the rotation of the dispenser head of the preferred embodiment required to obtain the maximum flow rate employed by most users, e.g., 10 cc/sec, should not and need not exceed about 120 degrees in order to obtain an entirely adequate sensitivity of adjustment and to not exceed the rotation comfortably obtainable with a continuous motion of the thumb and index finger. Conversely, a degree of rotation to obtain such typical maximum flow rate, if less than about 30 degrees, is too coarse for sensitive adjustment of the flow over the 1-10 cc/sec range of typical optimum flow rates defined previously. It should be apparent that the optimum relationship between flow rate and degree of head rotation can be obtained by selecting appropriate combinations of perforation orifice size, head diameter and fineness of threads on the cartridge (number of threads/inch).

In using the needle having the initial configuration shown in FIG. 4A it was found that an axial movement of the needle of only about 0.001 inch varies the gas flow from zero to the maximum required flow of 20 cc/sec. This corresponds to a dispenser head rotation of only about 10 degrees using the standard 28 threads per inch on commercial gas cartridges. While this arrangement gave acceptable flow adjustment for the initial tests, the 10 degree rotation is far less than the optimum rotation of 30 to 120 degrees defined above. Accordingly, an alternative dispenser head embodiment permitting use of finer threads, and an alternative needle configuration permitting a much larger axial motion, were incorporated into the preferred dispenser embodiment shown in FIG. 9B. A preferred feature of the subject invention, therefore, is the shape and size of the needle, and the extent and means for precise production and reliable repeated resealing of the perforation orifice by the needle, to obtain the optimum controllable flow rates in the defined effective and tolerable ranges.

Figure 9B:
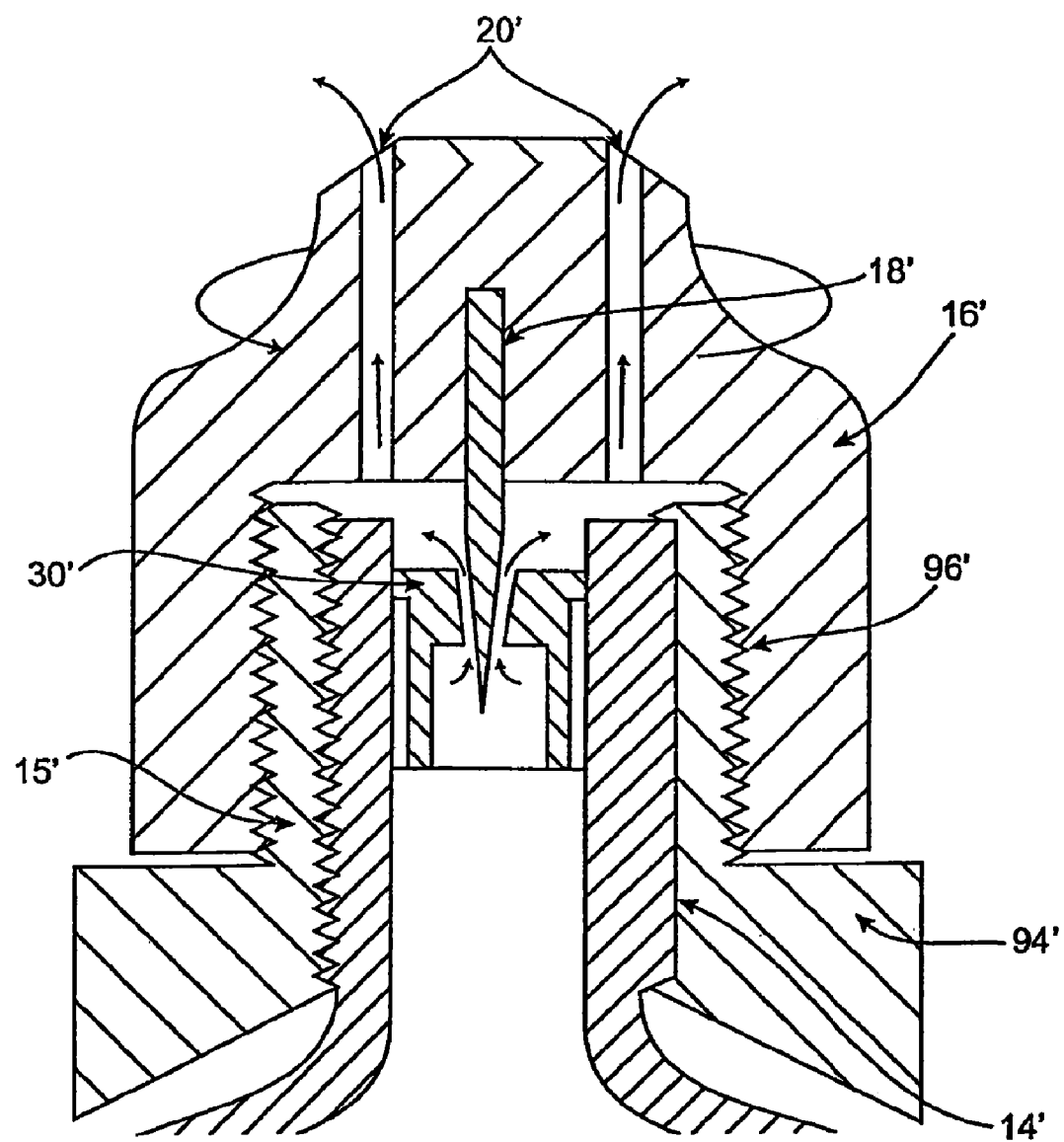
FIG. 9B illustrates a preferred two-piece dispenser head embodiment.

The preferred dispenser embodiment shown in FIG. 9B retains the major features of the initial embodiment described previously but, in addition, it can be seen that the single dispenser head part of the initial embodiment has been replaced by a two-part assembly consisting of a head 16' and a collar 94. The head 16' is similar to the initial dispenser head 16 in that it incorporates a perforating and flow-regulating needle 18' along with ports 20' for delivering the dispensed gas. The collar 94 is screwed onto the carbon dioxide cartridge neck 15' and fixed there against rotation, e.g. by a jam thread 14'. The head 16' is screwed onto a fine thread 96 on the collar. The fine thread 96 (e.g., 48-56 threads/inch) permits a much finer rotational adjustment than the coarse thread 14' (typically 28 threads/inch) on the cartridge neck.

Figure 4:
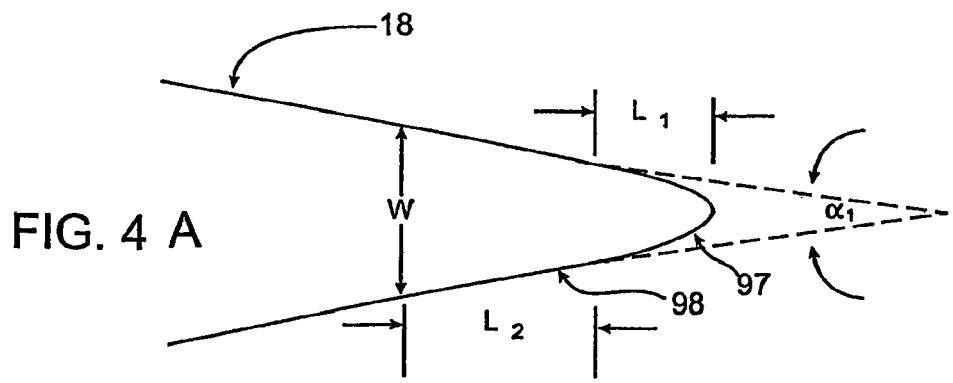
FIGS. 4A and 4B are detailed illustrations of the flow regulator needle of the dispenser head, showing exemplary dimensions for the initial and preferred needle configurations respectively.
FIG. 4C illustrates the analytical relationship between the critical needle taper angle $\alpha$ and the size of the annular orifice d for a needle displacement x.
Figure 4B:
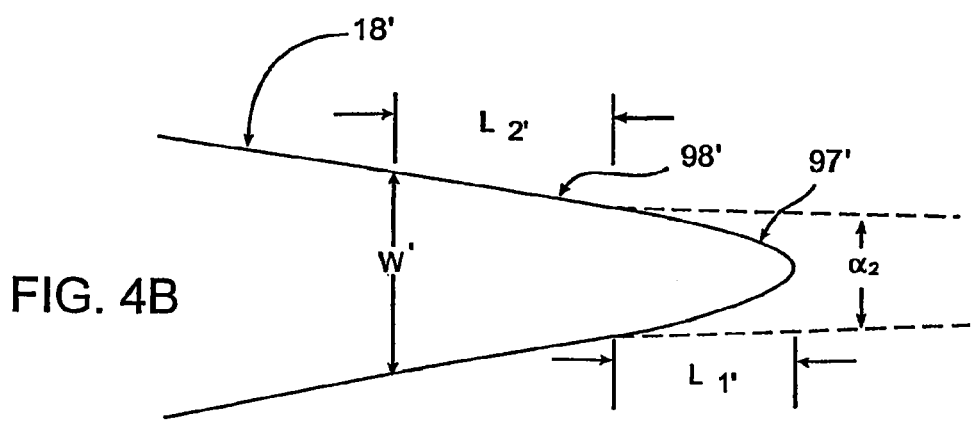

The preferred needle configuration, shown in FIG. 4B, permits obtaining the required very small change in orifice area by a relatively large axial displacement of the needle. The lower most portion of the needle, over a distance approximately equal to the thickness of the cartridge sealing cap 30, has essentially the same shape and size as the puncture point 97 shown in FIG. 4A as employed in the initial embodiment of the dispenser. The configuration of this point is an optimum compromise between the strength of a blunt point and the reduced force requirement of a sharp point in the puncture process. However, the needle region 98' beyond the puncture point, that is adjacent to the perforated cap wall, determines the size of the annular flow-controlling orifice of the valve seat 42 when the needle is partially withdrawn. The configuration of the flow-controlling seat region 98' of the needle is advantageous for obtaining the required flow regulation characteristics of the dispenser.

Figure 4C:
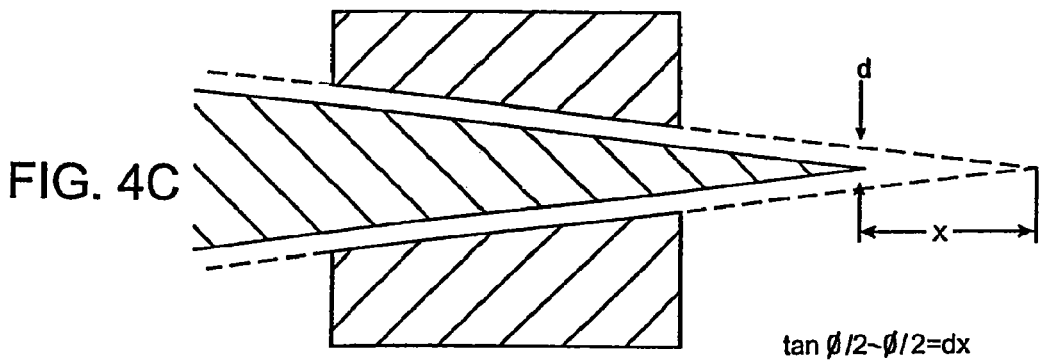

As shown analytically in FIG. 4C, the axial needle displacement giving a required size of the flow-controlling annular orifice is inversely dependent on the taper angle $\alpha$ of the needle in the seat region. This taper angle $\alpha$ is approximately 20 degrees in the initial needle configuration shown in FIG. 4A, which required a needle displacement x of about 0.001 inch between zero flow and full flow as obtained by a 10 degree rotation of the head with 28 threads/inch. To obtain the 120 degree optimum head rotation, the needle seat taper angle $\alpha$ therefore must be about 1.7 degrees for 28 threads/inch or about 3 degrees for the preferred 48 threads/inch.

Accordingly, exemplary dimensions for the needles 18 and 18' and cap 30 are set forth in Table II below and provide for desired flow rates in the range from 1 cc/sec to 20 cc/sec for cartridges 12 holding liquid carbon dioxide under pressure. It should be apparent that the preferred needle configuration shown in FIG. 4B, and the calibration and detent provisions shown in FIGS. 6-8, can be used with either the one-piece dispenser head shown in FIGS. 3A-3C and FIG. 7 or with the two-piece dispenser head shown in FIG. 9B to obtain its attendant advantages. It also should be noted that the two-piece preferred embodiment does not require detent slots in the cartridge threads 14', but only in the collar threads 96.

TABLE II

EXEMPLARY NEEDLE AND CAP DIMENSIONS

|  | Range | Specific |
|---|---|---|
| Needle 18: (FIG. 4A) | | |
| W | 0.4-0.6 mm | 0.50 mm |
| $\alpha$ | 15-25 deg | 20 deg |
| $L_1$ | 0.4-0.6 mm | 0.37 mm |
| $L_2$ | 0.4-0.6 mm | 0.37 mm |
| Needle 18': (FIG. 4B) | | |
| $W_1$ | 0.4-0.6 mm | 0.50 mm |
| $\alpha_1$ | 2-6 deg | 3.0 deg |
| $L_1'$ | 0.6-1.0 mm | 0.75 mm |
| $L_2'$ | 0.2-0.6 mm | 0.37 mm |
| Cap 30: (FIG. 5) | | |
| t | 0.25-0.4 mm | 0.30 mm |
| $\varnothing$ | 3.0-3.8 mm | 3.2 mm |

5. Embodiment with Separate Puncture and Valve Seal Mechanism. Referring now to FIG. 9A, an alternative dispenser head embodiment 80 will be described. The dispenser head 80 is similar to the embodiment described above with respect to FIGS. 1-5, except that the needle perforation and flow regulating aspects of the assembly are separated. In particular, the dispenser head 80 comprises a lower collar 82 and a flow-regulating cap 84 threadably mounted to an upper end of the lower collar. Needle 86 is secured in the lower portion of the flow-regulating cap 84 and includes two tapered regions. The first tapered region 88 acts as the needle tip which penetrates seal 90 which is mounted over the upper end 92 of a high pressure gas bottle 94. The seal 90 extends above a threaded neck 96 of the gas bottle 94. The lower collar 82 is threadably mounted over the threaded neck 96 in such a way that the seal 90 extends into a high pressure gas chamber 98 within the upper end of the lower collar 82. An O-ring seal 100 is provided to inhibit leakage of the high pressure gas.

Flow regulation in the dispenser head 80 is provided by the second tapered region 102 which is received in a valve seat 104 formed in the upper end of the lower collar 87. Rather than relying on needle penetration to form the flow control aperture, dispenser head 80 relies on a pre-formed conical valve seat 104 which mates with the tapered region 102 on the needle. In this way, the dimensions of both the seat 104 and the tapered region 102 may be carefully controlled in order to assure accurate gas flow control. Thus, when the flow regulating cap 84 is twisted to raise the cap relative to lower collar 82, the tapered region 102 will be lifted out of the valve seat 104. In this way, the flow regulation of the gas can be controlled. Additionally, sealing of the gas flow when the cartridge is to be turned off is provided by both seating of the tapered needle portion 102 in the seat 104 as well as seating of the needle tip in the penetration created in the seal 90. The use of the valve seat 90, which can be formed from a conventional hard metal, ceramic, or other valve material, can greatly enhance the useful life of the dispenser head 80. Thus, such designs may be particularly valuable for non-disposable units where the dispenser head 80 can be reused. Of course, the associated gas cartridge will be replaced whenever the gas being carried has been depleted.

6. Alternative Gas Provision Means. Referring now to FIG. 9, the methods of the present invention may also be performed with high volume systems in clinical, institutional, and chronic home-care settings. A large volume carbon dioxide or other gas bottle is provided and connected through a conventional pressure regulator 72. The output of the pressure regulator 72 will preferably pass through a gas-flow meter 74 and be connected by a suitable hose or tubing 76 to a hand-held dispenser nozzle 78. The nozzle 78 will have an outlet 79 adapted to interface with a nostril or mouth as described above for the hand-held embodiment. The nozzle 78 will typically also include a flow control valve, which may be essentially as illustrated in the earlier embodiments for the hand-held dispensers. The only difference required would be that, instead of being connected to a small carbon dioxide or other gas cartridge, the nozzle 78 may be connected to a much larger gas bottle 70 through flexible tube or hose 76, optionally with an in-line flow meter which allows the user to select and adjust a desired flow rate.

Figure 10:
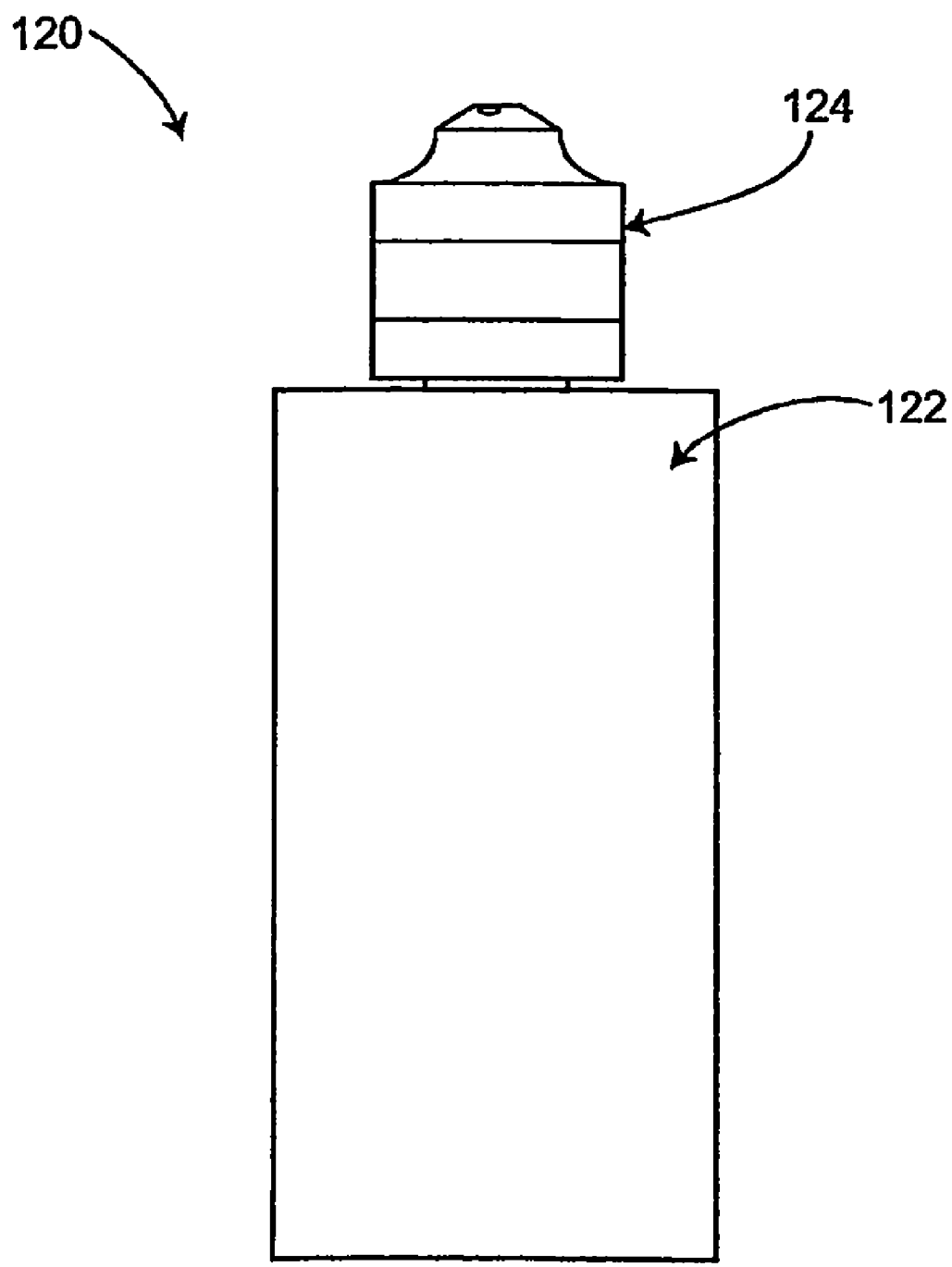
FIG. 10 illustrates an alternative hand-held dispenser employing a relatively low pressure gas source.
Figure 11:
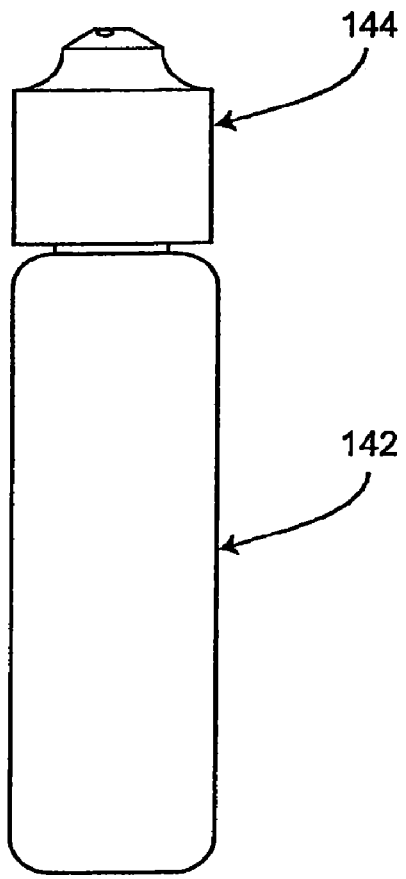
FIGS. 11 and 12 illustrate another alternate embodiment of the dispenser of the present invention, illustrating a chemical-gas generation system for producing gas according to the methods of the present invention.
Figure 12:
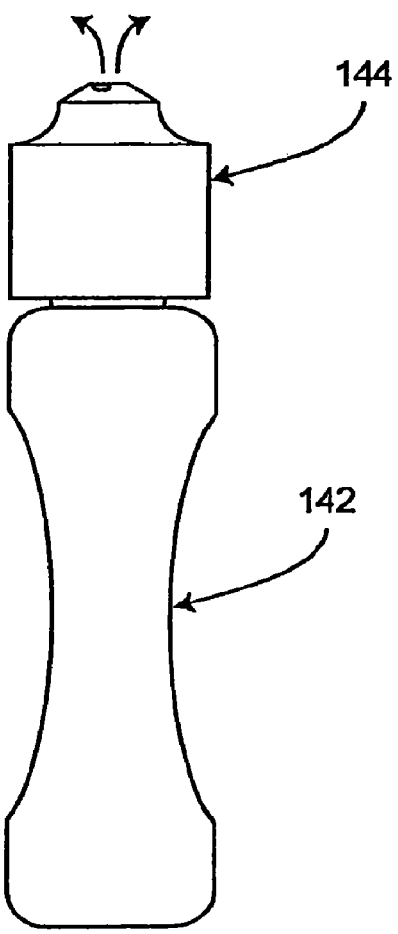

As described thus far, the embodiments of the dispensers of the present invention have relied on high pressure systems which contain liquid carbon dioxide or other therapeutic gas. Low pressure systems may be assembled in at least two ways. As shown in FIG. 10, a first exemplary low pressure system 120 may comprise a thin-walled container 122 which contains gaseous carbon dioxide or other therapeutic gas at a relatively low pressure, e.g., 100 psi. The containers 122 may be of the type conventionally employed for low pressure spray cans available for a variety of consumer uses. In contrast, the high pressure carbon dioxide cartridges described above will usually have an internal pressure of about 1,000 psi. The low pressure container 122 may be combined with a dispenser head 124 constructed generally as described above. The sizes of the flow passages, however, might be modified in order to accommodate the lower source pressures. In a second embodiment 140 carbon dioxide and other therapeutic gases may be provided at low pressures using a chemical generation system, as shown in FIGS. 11 and 12. For example, a container 142 may include reagents which, upon mixing, release carbon dioxide. In a particular embodiment, dry citric acid powder and sodium bicarbonate are disposed in the container 142 with separated water. The water is then mixed with the dry components, typically by crushing the container 142, as shown in FIG. 12. The water can be released in a variety of ways. For example, the water could be separated by a frangible barrier between the water and the dry components. Preferably, the water will be contained in frangible water-containing microcapsules so that the water is liberated as the container is crushed. The amount of water liberated, however, will depend on the degree to which the container 142 has been crushed, allowing a relatively long useful life for the system. As with prior systems, a dispenser head 144 having flow passages capable of selectively controlling the flow rate to the patient will be provided.

Figure 13:
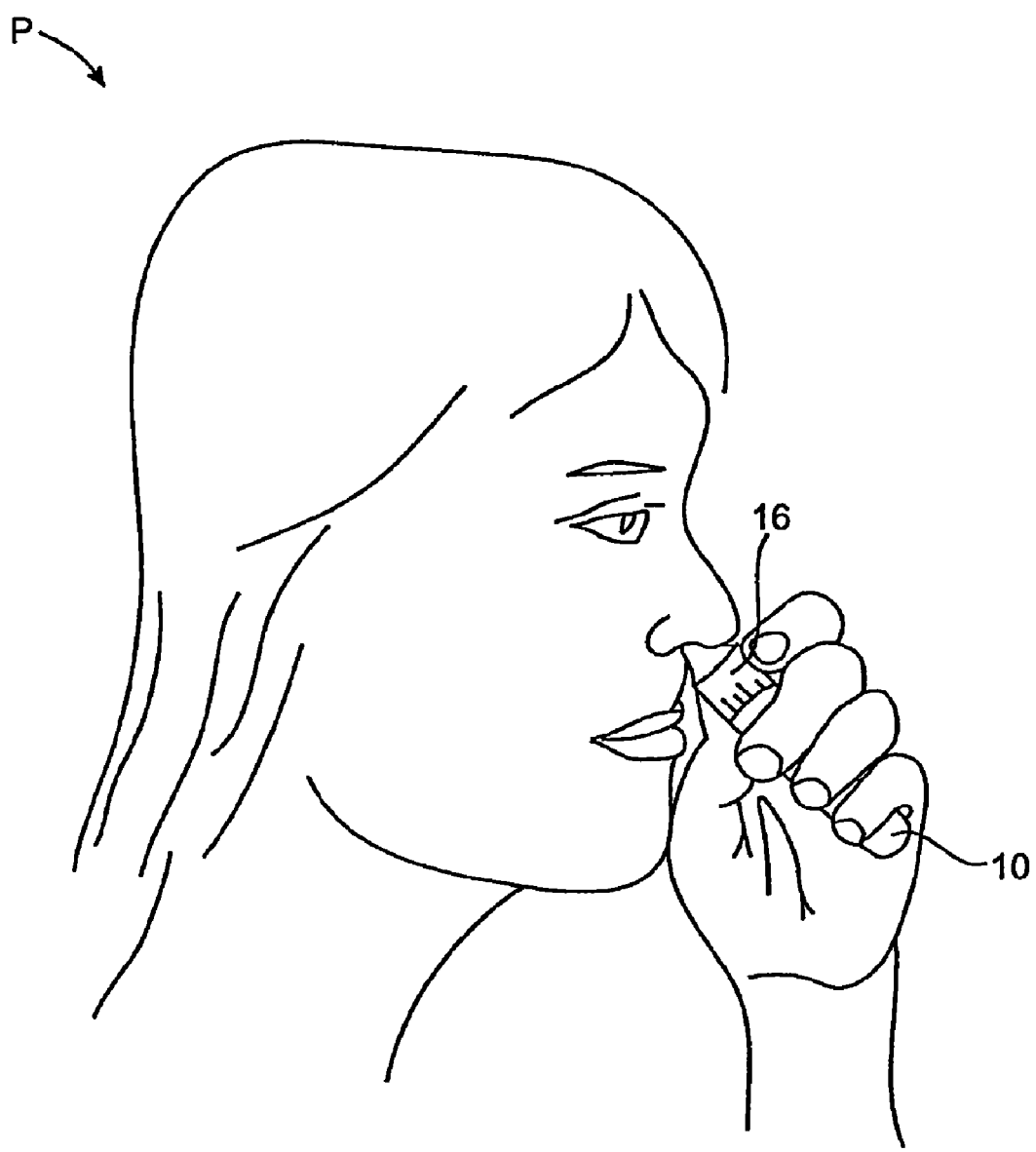
FIG. 13 illustrates a patient employing the dispenser of FIG. 1 for treatment of symptoms associated with common ailments.

7. Description of Use of the Dispenser Embodiments. Referring now to FIG. 13, any of the dispensers described above may be utilized by delivering the carbon dioxide or other therapeutic gas to the patient, either through the nose or through the mouth. As shown in FIG. 13, the dispensing head 16 of dispenser 10 is placed by the patient P into one nostril, while the patient refrains from inhaling the therapeutic gas, e.g., holds his/her breath. The carbon dioxide or other therapeutic gas from the dispenser 10 will thus infuse into the nostril, upwardly into the nasal passages and outward through the other nostril, preferably while the patient refrains from inhaling the therapeutic gas. Usually, the patient will keep his/her mouth closed during the nasal infusion, thus limiting the volume of the gas that infuses downward and through the mouth. In some instances, however, it may be desirable for the patient to open his/her mouth (while continuing to refrain from inhaling the therapeutic gas) so that the carbon dioxide or other therapeutic gas infuses not only through the nasal passages but downward through the throat and outward through the mouth. In this way, the mucous membranes of the nasal passages as well as the upper regions of the throat will be treated.

In other embodiments, the user may place the cartridge 10 into his/her mouth, permitting the carbon dioxide or other therapeutic gas to infuse upwardly through the throat and outward through the nostrils. Again, the patient will generally refrain from inhaling the therapeutic gas so that the treatment gas does not enter into the trachea or lungs. By limiting the regions being treated to the nasal passages and in some instances the nasal passages and upper regions of the throat, only very small volumes of the gas are required for treatment, and high (unbreathable) concentrations of the gas can be more effectively employed. This is particularly advantageous when hand-held systems are used where the amount of carbon dioxide or other treatment gas is limited. As noted in the examples provided below, it has been found that even very low volumes of carbon dioxide can be highly effective in treating a number of symptoms associated with the common ailments described above.

Figure 14:
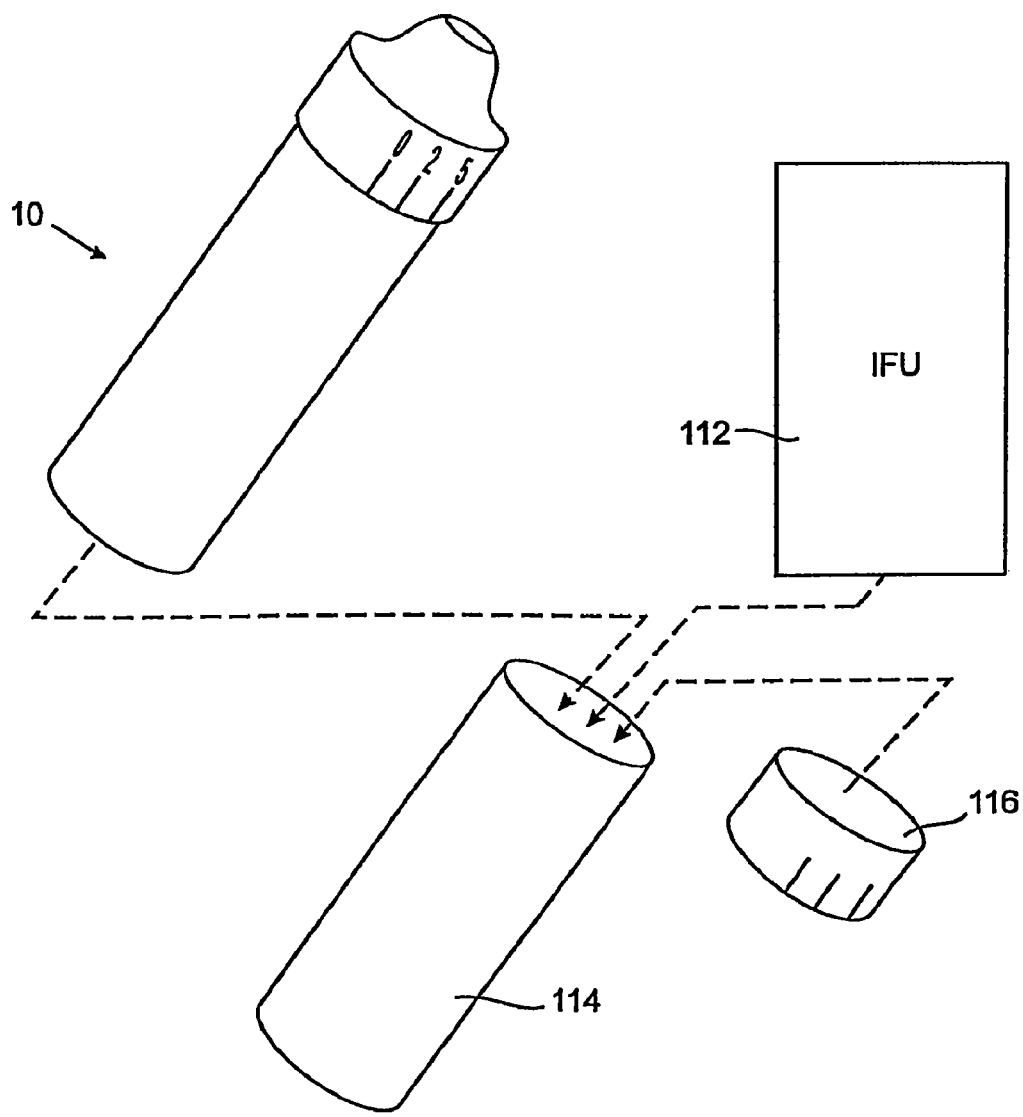
FIG. 14 illustrates a kit constructed in accordance with the principles of the present invention.

As shown in FIG. 14, kits according to the present invention will include a carbon dioxide or other therapeutic gas dispenser 10 in combination with instructions for use 12. The instructions for use will include written instructions corresponding to any of the methods of the present invention as described above. In particular, the written instructions will refer specifically to use of the cartridge 10 in a way to relieve symptoms of common ailments as described above. In addition to the cartridge 10 and written instructions 12, the kits will usually include packaging, for example in the form of a cylindrical container 114 having a removable cap 116. The dispenser 10 and instructions for use 112 will conveniently be packaged together within the container and covered by the cap 116.

The following examples are offered by way of illustration, not by way of limitation.

Experimental

1. Dispenser Models Constructed and Tested.

Figure 2:
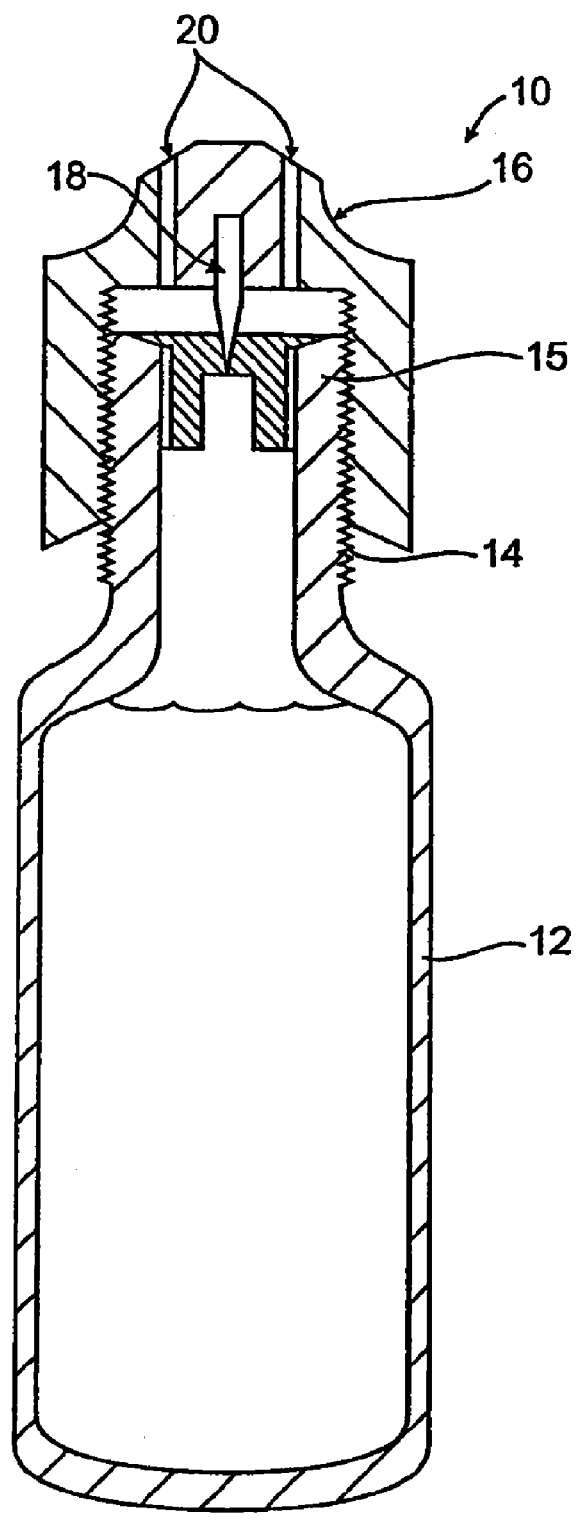
FIG. 2 is an axial cross-sectional view of an initial embodiment of the dispenser of FIG. 1.

Two models of the initial one-piece head embodiment shown in FIG. 2 were constructed and tested: one with the initial needle configuration shown in FIG. 4A and one with the preferred needle configuration shown in FIG. 4B. Similarly, two models of the preferred two-piece embodiment shown in FIG. 9B (with 48 threads/inch) were constructed and tested: one with the initial needle configuration shown in FIG. 4A and one with the preferred needle configuration shown in FIG. 4B. The dispenser heads were machined from Delrin plastic stock, with embedded needles machined from hardened carbon steel stock. Commercially available steel cartridges with threaded necks (28 threads/inch), containing 16 grams of carbon dioxide, were used in all models. The configurations of the needles were those shown in FIGS. 4A and 4B, with a 3 degree taper in the seat region 98' of the preferred needle configuration.

Figure 15:
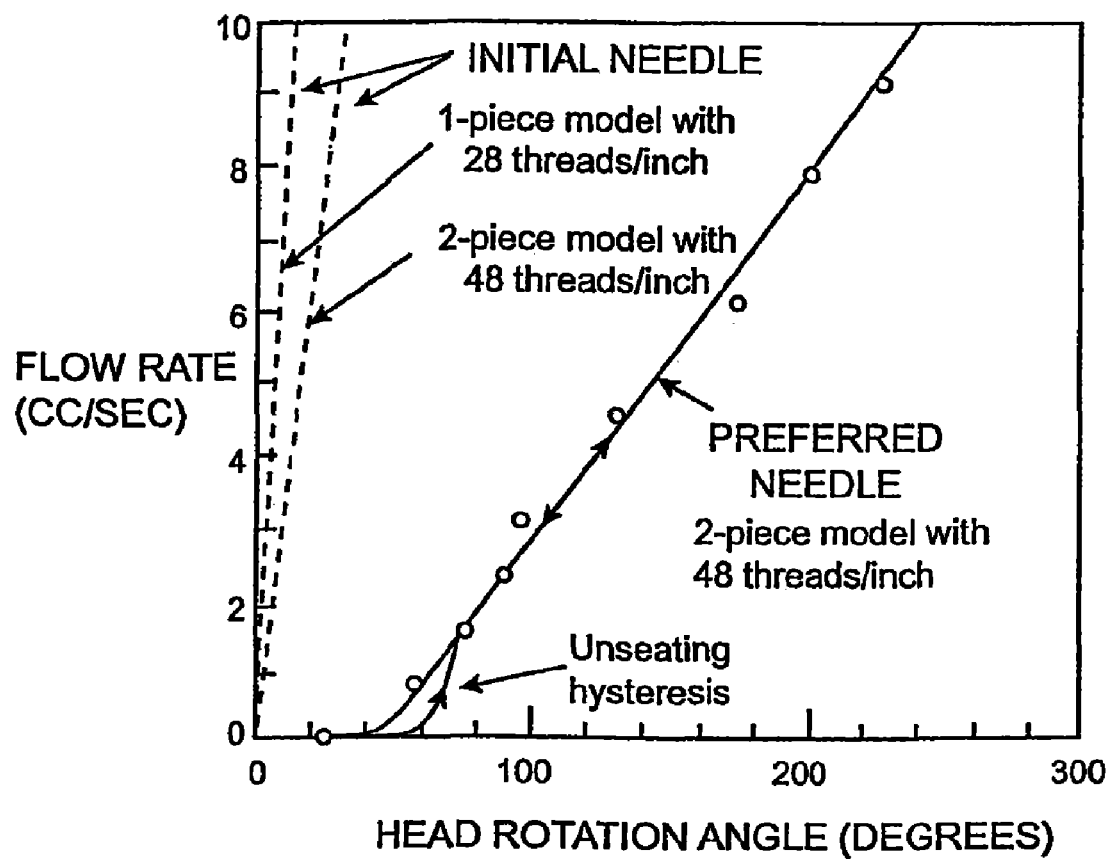
FIG. 15 is a graph comparing flow rate control sensitivity achieved with different needle designs.

FIG. 15 shows experimental measurements of the flow rate characteristics for the one-piece and two-piece embodiments with the initial needle configuration, as well as those for the combination of preferred two-piece dispenser head with the preferred needle configuration. Data obtained using the initial needle configuration was too erratic to be plotted, i.e., having large hysteresis and other non-reproducible flow characteristics. The dashed lines show the general sensitivity of flow rate to head rotation for those models, however. It can be seen that the preferred needle configuration 18' gives the greatly improved reproducible control and sensitivity required for self-treatment by the patient. The one-piece embodiments of the device of the present invention described above were used in these experiments.

2. Preliminary Human Application Tests

A. Materials and Methods

Test Device

The test device was a hand-held, multi-dose, disposable, dispenser that was approximately 3 to 4 inches long and ⅝ to ⅞ inches in diameter constructed as described above. The device consisted of a plastic twist-top flow regulator mounted on top of a pressurized steel cartridge containing liquid carbon dioxide. The tip of the flow regulator has a nosepiece that is the optimal size and configuration to place against and seal off a nostril for administration of the gas. In a number of subjects, the effective nasal and oral carbon dioxide flow rates, and maximum tolerable nasal and oral flow rates, were measured using a laboratory apparatus. This apparatus consisted of a flow regulator connected via tubing to a flow meter and a large tank of carbon dioxide. These flow data were used, together with the number of seconds gas was administered during therapy, to calculate the estimated dose of gas in milliliters.

Subjects

Of the total of 15 subjects included in the analysis, 11 used the treatment for 35 headaches and 9 subjects used it for 9 allergy attacks. Three subjects treated both headache and allergy but on different days. The subjects included adults, elderly, and children of both sexes in good general health, having mild, moderate, and severe headaches or having allergies to plant, animal, or airborne allergens. The device was used to treat migraine and tension-type headaches, jaw pain, and allergies (allergic rhinitis, with symptoms that included sinus congestion, sneezing, and itchy throat and eyes). There was no limitation on the duration of symptoms before treatment with the device. Subjects with no prior use of the device and those who have used it (to treat allergy symptoms) previously were included.

Transmucosal Treatment

Carbon dioxide (100%) was administered nasally by the subject for a few seconds via a nostril to fill the nasal passages while holding their breath, or taking breaths of room air occasionally if the dose was lengthy. The gas exited the other nostril. Such nasal administration is similar to presently marketed nasal inhalers except that the administered gas was not inhaled. Oral administration, via pursed lips with carbon dioxide exiting via the nostrils, was found to be more effective for allergic inflammation extending into the oral cavity. Subjects took as many doses as they needed for relief. It is important to note that there were no number of doses, duration of dose, time between doses, or gas flow rate specified for the user. Subjects chose their own regimen for symptom relief. Similarly, in medical practice today, gas therapy is a "titrate to effect" therapy without a specified dosage.

Outcome Measures

The International Headache Society (IHS) divides headache intensity into three categories: mild, moderate, and severe. The rating of the intensity level depends on the extent to which the headache interferes with the ability to function. Mild headaches do not interfere with the ability to function, moderate headaches interfere with the ability to function but do not require bed rest, and severe headaches are incapacitating and require bed rest. The IHS uses headache relief at two hours as its primary outcome measure for present-day headache drug studies. Since therapy of the present invention acts much faster than present-day drugs, the primary outcome measure selected for this analysis was headache relief at 30 minutes. Each of the headache outcome measures used for this analysis is as follows:

Headache relief efficacy at 1, 5, 15, and 30 minutes post-treatment—headache relief efficacy is obtained when a pre-treatment headache severity of mild, moderate, or severe severity is improved to a post-treatment severity of none, mild, or moderate respectively.

Headache free efficacy at 1, 5, 15, and 30 minutes post-treatment—headache free efficacy is obtained when a pre-treatment headache of mild, moderate, or severe severity is improved to a post-treatment severity of none.

Headache recurrence within 24 hours post-treatment—recurrence within 24 hours is defined as no or mild headache severity after treatment that then worsened to moderate or severe headache severity within 24 hours after treatment with no use of rescue medication before the worsening.

Safety parameter—safety is defined as no adverse after-effects of treatment.

For allergy, the rating of the intensity level depends on the extent to which the allergy interferes with the ability to function. Mild allergies do not interfere with the ability to function, moderate allergies interfere with the ability to function but do not completely disrupt the function, and severe allergies are incapacitating and completely disrupt the ability to function. The same outcome measures as for headache were used for allergy.

B. Results and Discussion

Dosage

Initially, the effective nasal and oral, and maximum tolerable nasal and oral carbon dioxide flow rates were measured in seven subjects using a laboratory apparatus. The flow rate selected that is effective or the maximum tolerable rate varies with the individual. At low flow rates, the presence of the carbon dioxide produces a "tingling" sensation similar to that produced during drinking of carbonated beverages that inadvertently enter the nasal passages e.g., "bubbles up the nose". This is the effective rate and the tingling is a welcome sensation because it usually coincides with immediate relief of symptoms. Above a certain subjectively determined flow rate the sensation becomes unpleasant, which may be described as a "stinging" or "burning" sensation. At a still higher flow rate (maximum tolerable rate), the stinging sensation becomes intolerable and subjects remove the device from their nostril. Also, subjects are more sensitive to the first dose of a series for one attack; subsequent doses give less or no sensation. The flow data show that lower effective and maximum tolerable flow rates were selected by subjects having no prior experience with the treatment (see Table III below). High flow rates were better tolerated orally than nasally. The typical effective rate nasally was 1 to 5 ml/sec and 5 to 10 ml/sec orally.

TABLE III

EFFECTIVE AND MAXIMUM TOLERABLE CARBON DIOXIDE FLOW RATES

| Age (yrs) | Gender (m/f) | Experience w/ Device (#) | Effective Nasal Rate (ml/sec) | Max Tolerable Nasal Rate (ml/sec) | Effective Oral Rate (ml/sec) | Max Tolerable Oral Rate (ml/sec) |
|---|---|---|---|---|---|---|
| 43 | f | 0 | <1 <1 | <1 | >10* | >10* |
| 47 | f | 0 | <1 | 2 | 5-10 | >10* |
| 9 | m | 0 | 1-2 | 3 | 5-10 | >10* |
| 44 | m | 0 | 2 | 4 | 2 | >10* |
| 45 | m | >10 | 4-5 | 10 | 5-10 | >10* |
| 72 | m | >1000 | 4-5 | 10 | 5-10 | >10* |
| 72 | f | >1000 | 4-5 | 10 | 5-10 | >10* |

*Maximum calibrated flow rate of flow meter was 10 ml/sec

For therapy, it is important to note that no number of doses, duration of dose, time between doses, or gas flow rates were specified for the user. Subjects chose their own regimen for symptom relief. Analysis of the therapy data (see Table IV below) shows that the treatment is dose dependent. In general, milder attacks required fewer doses of shorter duration, thus a lower volume of gas, than severe attacks. Also, tension-type headaches required shorter average duration doses than migraine headaches (tension=24 sec, range=6-56 sec; migraine=57 sec, range=30-83 sec), and generally a lower volume of gas (tension=122 ml, range=28-288 ml; migraine=158 ml, range=82-233 ml). The average duration and total dose volume for headache and allergy treatment were similar (headache=32 sec and 124 ml; allergy=39 sec and 133 ml) as were the total treatment times (headache=7 mm; allergy=5 min).

hours for tension-type headaches™ The subjects with migraines had used the device from 0 to 8 times and those with tension-type headache from 0 to 13 times with one individual who had not used it previously for headache but has used it for allergies over 1000 times™

Using the efficacy outcome measures defined above, (which include mild headaches, with relief defined as mild, moderate, or severe reduced to none, mild, or moderate respectively) the present treatment had a 94% headache relief efficacy (migraine=90%, tension=96%) and an 80% headache free efficacy (migraine=90%, tension=80%) for headaches at 30 minutes post-treatment (see Table V below). Con-

TABLE IV

EFFECTIVE CARBON DIOXIDE DOSE

| Attack Type, Severity (N = No. of Subjects) | No. of Attacks (n) | Single Dose Duration (sec) | Number of Doses (#) | Total Dose (sec) | Est. Rate (ml/sec) | Est. Total Dose (ml) | Total Treatment Time (min) |
|---|---|---|---|---|---|---|---|
| Headache (N = 11) | | | | | | | |
| Migraine-Mild | 6 | 23 | 1 | 30 | 3 | 82 | 1 |
| Migraine-Severe | 4 | 35 | 2 | 83 | 3 | 233 | 28 |
| Migraine-All | 10 | 29 | 2 | 57 | 3 | 158 | 15 |
| Tension-Mild | 3 | 3 | 2 | 6 | 3 | 28 | 2 |
| Tension-Moderate | 15 | 6 | 2 | 11 | 4 | 50 | 4 |
| Tension-Severe | 7 | 15 | 4 | 56 | 5 | 288 | 11 |
| Tension-All | 25 | 8 | 3 | 24 | 4 | 122 | 6 |
| Headache-All | 35 | 15 | 2 | 32 | 4 | 124 | 7 |
| Allergy (N = 9) | | | | | | | |
| Allergy-Mild | 1 | 15 | 2 | 40 | 5 | 200 | >0.7 |
| Allergy-Moderate | 2 | 3 | 2 | 16 | 2 | 31 | >0.2 |
| Allergy-Severe | 6 | 17 | 2 | 46 | 4 | 156 | >3.9 |
| Allergy-All | 9 | 13 | 2 | 39 | 3 | 133 | 5 | siderable headache relief was also obtained at 15 minutes post-treatment (headache relief efficacy=86%; headache free efficacy=74%). Subjects reported immediate onset of symptom relief within seconds while administering the first dose. There were no instances of headache recurrence 24 hours post-treatment with the gas therapy and no subjects reported any adverse after effects of treatment.

TABLE V

EFFICACY AND SAFETY - HEADACHE (MILD, MODERATE, SEVERE)

| Attack Type (N = No. of subjects) | No. of Attacks (n) | Symptom Relief, Minutes Post-Treatment (%) | | | | Symptom Free, Minutes Post-Treatment (%) | | | | 24-hr. Recur Rate (%) | After Effects (%) |
|---|---|---|---|---|---|---|---|---|---|---|---|
| | | 1 | 5 | 15 | 30 | 1 | 5 | 15 | 30 | | |
| Migraine (N = 2) | 10 | 60 | 60 | 60 | 90 | 60 | 60 | 60 | 90 | 0 | 0 |
| Tension (N = 9) | 25 | 20 | 64 | 96 | 96 | 20 | 64 | 80 | 80 | 0 | 0 |
| Headache-All | 35 | 31 | 63 | 86 | 94 | 31 | 60 | 74 | 80 | 0 | 0 |

Headache

A total of 11 headache subjects with 35 headaches were assessed™ The subjects were males (49%) and females (51%) ranging in age from 9 to 73 years (mean=55) with mild (26%), moderate (43%), and severe (31%) headaches which included migraine (29%), tension-type (66%), and jaw headaches (5%). Headache duration before treatment averaged 2 hours (migraine=2.4 hours, tension=1.5 hours) and ranged from 0.3 to greater than 18 hours for migraines and 0.1 to 4

Using the more stringent IHS efficacy outcome measures (that exclude mild headaches, with relief defined as moderate or severe reduced to mild or none) the treatment had the same average symptom headache free efficacy of 80% (migraine=75%, tension=80%) for headache at 30 minutes as in the above analysis (see Table VI below). With these criteria, the treatment had an 84% headache relief efficacy (migraine=100%, tension=77%) for headache at 30 minutes.

Considerable headache relief also was obtained at 15 minutes post-treatment (headache relief efficacy=72%; headache free efficacy=72%).

TABLE VI

EFFICACY AND SAFETY - HEADACHE
(MODERATE, SEVERE - IHS CRITERIA)

| Attack Type (N = No. of subjects) | No. of Attacks (n) | Symptom, Relief, Minutes Post-Treatment (%) | | | | Symptom Free, Minutes Post-Treatment (%) | | | | 24-hr. Recur Rate (%) | After Effects (%) |
|---|---|---|---|---|---|---|---|---|---|---|---|
| | | 1 | 5 | 15 | 30 | 1 | 5 | 15 | 30 | | |
| Migraine (N = 2) | 4 | 25 | 25 | 25 | 100 | 25 | 25 | 25 | 75 | 0 | 0 |
| Tension (N = 8) | 22 | 14 | 55 | 77 | 77 | 14 | 55 | 77 | 77 | 0 | 0 |
| Headache-All | 25 | 16 | 52 | 72 | 84 | 16 | 52 | 72 | 80 | 0 | 0 |

In summary, treatment of migraine and tension-type headache according to the present invention shows 80-94% efficacy occurring in seconds to minutes (average treatment time=7 min) compared to 50-70% efficacy in 2-4 hours with current drugs even though this was a dose-finding analysis where the optimal dosing regimen was not defined. This feasibility summary had many subjects who had never used the device, or never used it for headaches, resulting in a number of instances where therapy was more efficacious after they learned the most effective personal dosing regimen. For example, a subject suffering severe tension headaches tried on three occasions to eliminate the headaches with only moderate success using numerous doses of short duration (six doses of 8 sec each=240 ml). Subsequently, she was able to completely eliminate a severe tension headache and a severe jaw/tooth ache with fewer doses of longer duration (three doses of 15 sec each=225 ml and three doses of 45 sec each=675 ml, respectively). As another example, a subject suffering a moderate tension headache, who had never used the device for headaches, tried to eliminate the headache with no success using an extremely small dose (one dose of 1 sec=2 ml). Finally, one patient suffering from a migraine headache was unable to improve on a mild migraine the first time he used the device (one dose for 30 sec=60 ml). However, he was able to completely eliminate all subsequent mild and severe migraines with a dosage regimen he developed that increased the gas volume dose (two to three doses for 25 sec each=120 ml). He had a history of severe migraines bimonthly for over 25 years and had selected sumatriptan (Imitrex®) by injection as a treatment prior to receiving the device. Since he has tested the device of the present invention, he has used no other headache medication and no longer has moderate or severe migraines. When he first feels the onset of a migraine, he doses twice for 20 to 25 seconds according to the present invention. This completely aborts the migraine and it does not recur. The frequency of migraine incidents has also decreased.

Allergy

There were 9 allergy subjects with 9 allergy attacks assessed. The subjects were males (67%) and (33%) females ranging in age from 9 to 72 years (mean=39) with mild (11%), moderate (22%), and severe (67%) allergies which included symptoms in the nose, throat, and eyes). Allergy duration before treatment ranged from 0.2 to 1.5 hours. The subjects had used the device from 0 to over 1000 times.

The treatment achieved 100% allergy relief efficacy and an 89% allergy free efficacy at both 15 and at 30 minutes (see Table VII below). Using the more stringent efficacy outcome measures (which exclude mild allergies and relief is defined as moderate or severe reduced to mild or none) the treatment had essentially the same allergy relief efficacy and allergy free efficacy as in the above analysis. Subjects reported immediate onset of symptom relief within seconds while administering the first dose. There was a 50% recurrence of allergy symptoms; however, N was small (N=4) for this determination. The recurrences did not occur until 3 hours or longer post-treatment.

TABLE VII

EFFICACY AND SAFETY - ALLERGY (MILD, MODERATE,
SEVERE AND MODERATE, SEVERE)

| Symptom Type | No. of Attacks (n) | Symptom, Relief, Minutes Post-Treatment (%) | | | | Symptom Free, Minutes Post-Treatment (%) | | | | 24-hr. Recur Rate (%) | After Effects (%) |
|---|---|---|---|---|---|---|---|---|---|---|---|
| | | 1 | 5 | 15 | 30 | 1 | 5 | 15 | 30 | | |
| Allergy (N = 9) | 9 | 33 | 78 | 100 | 100 | 33 | 67 | 89 | 89 | 50 | 0 |
| Allergy (N = 8)* | 8 | 25 | 75 | 100 | 100 | 25 | 63 | 88 | 88 | 50 | 0 |

*More stringent outcome measure definitions

In summary, treatment of allergic rhinitis according to the present invention shows 88-100% efficacy occurring in seconds to minutes (average treatment time=5 min) compared to minutes to hours with current drugs. No subjects reported any adverse after effects of treatment.

While the above is a complete description of the preferred embodiments of the invention, various alternatives, modifications, and equivalents may be used. Therefore, the above description should not be taken as limiting the scope of the invention that is defined by the appended claims.

What is claimed is:

1. A method for treating rhinitis or conjunctivitis in a patient in need thereof, said method comprising:
   releasing from a hand-held dispenser a therapeutic, non-inhaled, dosage of a gas comprising carbon dioxide, wherein the hand-held dispenser is a multi-dose dispenser comprising a nosepiece and a flow regulator, the flow regulator comprising a flow-controlling orifice, and the hand-held dispenser configured to receive a carbon dioxide cartridge, wherein the gas is released from the nosepiece, and wherein the therapeutic dosage of the gas is accomplished at a flow rate from 1 cc/sec to 20 cc/sec for a duration of 2-30 seconds per nostril, the flow rate being repeatably controlled by the flow regulator; and
   instructing the patient to substantially refrain from inhaling while the gas is being released.

2. The method of claim 1, wherein the hand held dispenser is a two-piece dispenser.

3. The method of claim 1, wherein the flow rate is selected by the patient.

4. The method of claim 3, wherein the hand-held dispenser is a one-piece dispenser.

5. The method of claim 1, wherein the hand-held dispenser further comprises a pressure regulator.

6. The method of claim 1, wherein the duration is 5-10 seconds per nostril.

7. The method of claim 1, wherein the duration is 2-15 seconds per nostril.

8. The method of claim 1, wherein the dose is repeated from 1 to 10 times.

9. The method of claim 1, wherein the method is for treating conjunctivitis.

10. The method of claim 1, wherein the method if for treating rhinitis and the rhinitis is allergic rhinitis.

11. The method of claim 1, wherein the flow rate is from 2 cc/sec to 10 cc/sec.

12. The method of claim 1, wherein the flow rate is from 1 cc/sec to 5 cc/sec.

13. The method of claim 1, wherein the flow rate is from 4 cc/sec to 5 cc/sec.

14. The method of claim 1, wherein the flow rate is 10 cc/sec.

15. The method of claim 1, wherein the gas comprises at least 50% carbon dioxide.

16. The method of claim 1, wherein the gas comprises at least 70% carbon dioxide.

17. The method of claim 1, wherein the gas comprises at least 95% carbon dioxide.

18. The method of claim 1, wherein the gas comprises substantially pure carbon dioxide.

* * * * *